(12) United States Patent
Benesh et al.

(10) Patent No.: US 7,396,943 B2
(45) Date of Patent: Jul. 8, 2008

(54) OPIOID RECEPTOR ANTAGONISTS

(75) Inventors: Dana Rae Benesh, Westfield, IN (US); Maria Jesus Blanco-Pillado, Indianapolis, IN (US); Charles Howard Mitch, Columbus, IN (US); Kumiko Takeuchi, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 583 days.

(21) Appl. No.: 10/544,286

(22) PCT Filed: Mar. 1, 2004

(86) PCT No.: PCT/US2004/003368

§ 371 (c)(1),
(2), (4) Date: Aug. 2, 2005

(87) PCT Pub. No.: WO2004/080996

PCT Pub. Date: Sep. 23, 2004

(65) Prior Publication Data

US 2006/0166987 A1    Jul. 27, 2006

(51) Int. Cl.
*C07D 327/04*    (2006.01)
*C07D 277/04*    (2006.01)

(52) U.S. Cl. ......................... 549/29; 548/146

(58) Field of Classification Search .................. None
See application file for complete search history.

(56) References Cited

U.S. PATENT DOCUMENTS 4,891,379 A    1/1990    Zimmerman et al.

FOREIGN PATENT DOCUMENTS

| WO | WO 00/40560 | 7/2000 |
|----|-------------|--------|
| WO | WO 02/050071 | 7/2002 |
| WO | WO 02/078693 | 10/2002 |

*Primary Examiner*—Cecilia Tsang
*Assistant Examiner*—Savitha Rao
(74) *Attorney, Agent, or Firm*—John C. Demeter; Francis O. Ginah

(57) ABSTRACT

A compound of the formula I: (I) wherein the variables are as described herein, or a pharmaceutically acceptable salt, solvate, enantiomer, racemate, diastereomer or mixture thereof, formulations and methods of use thereof are disclosed.

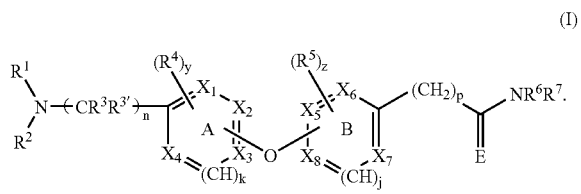

(I)

2 Claims, No Drawings

OPIOID RECEPTOR ANTAGONISTS

The present invention is in the field of medicinal chemistry. The invention relates specifically to compounds useful as opioid antagonists, methods of treatment, methods of using, and pharmaceutical compositions thereof.

BACKGROUND

Three types of opioid receptors, mu, kappa, and delta opioid receptors are generally reported. Recent evidence points to the interactions between receptor dimer combinations of mu, kappa and/or delta receptors (called heterodimers) as also contributing to opioid activity. Opioid receptors and their normal regulation or lack thereof, has been implicated in disease states including irritable bowel syndrome, nausea, vomiting, pruritic dermatoses, depression, smoking and alcohol addiction, sexual dysfunction, stroke and trauma in animals. Therefore it is not surprising that the ability to antagonistically bind opioid receptors has been shown to produce ameliorative, preventative and/or treatment effects in animals including humans afflicted with one or more of these disease states.

More recently, antagonists of the opioid receptors have been found to increase metabolic energy consumption, and reduction of weight in obese rats while maintaining muscle mass. These findings indicate that an effective opioid antagonist may be useful in preventing, treating and/or ameliorating the effect of obesity. Considering the percentage of the population that is obese in Western societies and the indirect costs associated with treating the effects and symptoms of obesity and Related Diseases, the importance of these findings cannot be overstated.

Though many opioid antagonists have been disclosed, the search continues for alternative and/or improved or more effective antagonists having an overall benefit to the patient with little or no major side effects. U.S. Pat. No. 4,891,379 disclosed and claimed phenylpiperidine opioid antagonists useful for the treatment of diabetes and obesity. In particular, U.S. Pat. No. 4,891,379 disclosed the compound LY 255582 represented by the structure

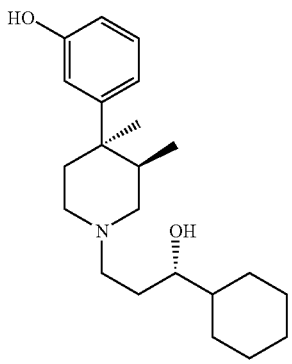

U.S. Pat. No. 4,191,771 also disclosed and claimed compounds useful as opioid antagonists. Also, bicyclic analogs of phenyl piperidine have been prepared and reported as opioid antagonists in Wentland, et al., *Biorganic and Medicinal Chemistry Letters* 11 (2001) 623-626; see also Wentland, et al., *Bioorganic and Medicinal Chemistry Letters* 11 (2001) 1717-1721. Finally, European Patent application number EP 1 072592A2 filed May 18, 2000, discloses phenylpiperidine compounds of formula I

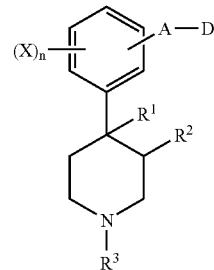

wherein A, D, $R^1$, $R^2$, $R^3$ X, and n have meanings given in the description, which are useful in the prophylaxis and in the treatment of diseases mediated by opioid receptors such as pruritus.

Regardless of these and other disclosures of compounds useful as opioid receptor antagonists, there remains an unmet medical need for a safe, effective and/or alternate treatment or prophylaxis of diseases associated with opioid receptors, particularly obesity and Related Diseases.

SUMMARY OF THE INVENTION

The present invention provides a compound of the formula (I)

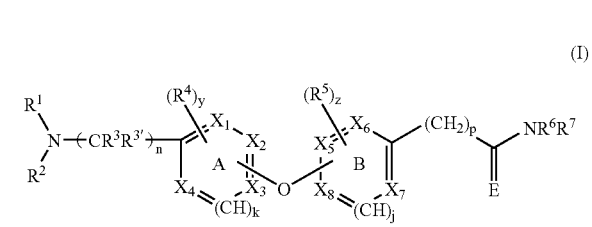

wherein when K is 0, one of $X_1$, $X_2$, $X_3$, $X_4$, is a S or O atom and the others are independently selected from C, CH, or N; and wherein when j is 0, one of $X_5$, $X_6$, $X_7$, and $X_8$ is S, or O, and the others are independently selected from C, CH, or N; provided that both k and j are not simultaneously equal to zero or 1; and provided that each of rings A or B has no more than 2 nitrogen atoms; and provided that double bonds in the rings are present or absent as needed to maintain appropriate valency;

n is 0, 1, 2, or 3;

k is 0 or 1; j is 0 or 1;

p is 0, 1 or 2;

E is O or NH;

$R^1$ and $R^2$ are independently selected from hydrogen, $C_1$-$C_8$ alkyl, $C_2$-$C_8$ alkenyl, $C_2$-$C_8$ alkynyl, phenyl, $C_1$-$C_{10}$ alkylaryl, C(O)$C_1$-$C_8$ alkyl, CO(O)$C_1$-$C_8$alkyl, $SO_2C_1$-$C_8$ alkyl, $SO_2C_1$-$C_{10}$ alkylaryl, or $SO_2C_1$-$C_8$ alkylheterocyclic, $C_4$-$C_{10}$ alkylcycloalkane, $C_1$-$C_8$ alkoxyalkyl, $(CH_2)_n$C(O)$OR^8$, $(CH_2)_nC(O)R^8$, $(CH_2)_mC(O)NR^8R^8$, and $(CH_2)_m NSO_2R^8$; wherein each of the alkyl, alkenyl, and aryl groups are optionally substituted with one to five groups independently selected from $C_1$-$C_8$ alkyl, $C_2$-$C_8$ alkenyl, phenyl, $C_1$-$C_8$ alkylaryl, C(O)$C_1$-$C_8$ alkyl, CO(O) $C_1$-$C_8$ alkyl $C_1$-$C_8$ alkoxy, $SO_2C_1$-$C_8$ alkyl, $SO_2C_1$-$C_8$ alkylaryl, $SO_2C_1$-$C_8$ alkylheterocyclic, $C_4$-$C_{10}$ alkylcycloalkane, $(CH_2)_nC(O)OR^8$, $(CH_2)_nC(O)R^8$; and wherein $R^1$ and $R^2$ may optionally combine with each other to form a 4, 5, 6, or 7-member nitrogen-containing heterocycle which nitrogen-containing heterocycle may have substituents selected from the group consisting of oxo, amino, $C_1$-$C_8$ alkyl, $C_2$-$C_8$ alkenyl, $C_2$-$C_8$ alkynyl, phenyl, $C_1$-$C_8$ alkylaryl, $C(O)C_1$-$C_8$ alkyl, $CO(O)C_1$-$C_8$ alkyl, halo, $C_1$-$C_8$ haloalkyl;

$R^3$ and $R^{3'}$ are each independently selected from Hydrogen, $C_1$-$C_8$ alkyl, $C_2$-$C_8$ alkenyl, $C_2$-$C_8$ alkynyl, $C_1$-$C_8$ alkoxy, $C_1$-$C_8$ thioalkyl, phenyl, aryl, $C_1$-$C_8$ alkylaryl;

$R^4$ and $R^5$ are each independently selected from Hydrogen, $C_1$-$C_8$ alkyl, $C_2$-$C_8$ alkenyl, $C_2$-$C_8$ alkynyl, $C_1$-$C_8$ alkoxy, halo, $C_1$-$C_8$ haloalkyl, phenyl, aryl, $C_1$-$C_8$ alkylaryl, $(CH_2)_m$ $NSO_2C_1$-$C_8$ alkyl, $(CH_2)_m NSO_2$phenyl, $(CH_2)_m NSO_2$aryl, —$C(O)C_1$-$C_8$ alkyl, or —$C(O)OC_1$-$C_8$ alkyl; wherein each $R^4$ or $R^5$ is attached to its respective ring only at carbon atoms, and wherein y is 0, 1, 2, or 3; and wherein z is 0, 1, 2, or 3;

$R^6$ and $R^7$ are each independently selected from hydrogen, $C_1$-$C_8$ alkyl, $C_2$-$C_8$ alkenyl, $C_2$-$C_8$ alkynyl, $C(O)C_1$-$C_8$ alkyl, hydroxy, $C_1$-$C_8$ alkoxy, $SO_2C_1$-$C_8$ alkyl, $SO_2C_1$-$C_8$ alkylaryl, or $SO_2C_1$-$C_8$ alkylheterocyclic, aryl, $C_1$-$C_8$ alkylaryl, $C_3$-$C_7$ cycloalkane, $C_1$-$C_{10}$ alkylcycloalkane, $(CH_2)_n C(O)OR^8$, $(CH_2)_n C(O)R^8$, $(CH_2)_m C(O)NR^8R^8$, and $(CH_2)_m$ $NSO_2R^8$; wherein each of the alkyl, alkenyl, and aryl groups are optionally substituted with one to five groups independently selected from $C_1$-$C_8$ alkyl, $C_2$-$C_8$ alkenyl, phenyl, and $C_1$-$C_8$ alkylaryl; and wherein $R^6$ and $R^7$ may independently combine together, and with the nitrogen atom to which they are attached or with 0, 1, or 2 atoms adjacent to the nitrogen atom to which they are attached to form a 4, 5, 6, or 7-membered nitrogen containing heterocycle which nitrogen containing heterocycle may further have substituents selected from the group consisting of oxo, amino, $C_1$-$C_8$ alkyl, $C_2$-$C_8$ alkenyl, $C_2$-$C_8$ alkynyl, phenyl, $C_1$-$C_8$ alkylaryl, $C(O)C_1$-$C_8$ alkyl, $C(O)O C_1$-$C_8$ alkyl, hydroxy, $C_1$-$C_8$ alkoxy, halo, and haloalkyl;

$R^8$ is hydrogen, $C_1$-$C_8$ alkyl, $C_2$-$C_8$ alkenyl, $C_5$-$C_8$ alkylaryl, —$C(O)C_1$-$C_8$ alkyl, or —$C(O)OC_1$-$C_8$ alkyl; m is 1, 2, or 3; or a pharmaceutically acceptable salt, solvate, enantiomer, racemate, diastereomers or mixtures thereof.

The present invention also provides a method for the prevention, treatment and/or amelioration of the symptoms of obesity and Related Diseases comprising administering a therapeutically effective amount of a compound of formula I to a patient in need thereof.

The present invention also provides a pharmaceutical formulation comprising a compound of formula I in association with a carrier, diluent and/or excipient.

The present invention also relates to a method for the treatment and/or prophylaxis of obesity and Related Diseases including eating disorders (bulimia, anorexia nervosa, etc.), diabetes, diabetic complications, diabetic retinopathy, sexual/reproductive disorders, depression, anxiety, epileptic seizure, hypertension, cerebral hemorrhage, congestive heart failure, sleeping disorders, atherosclerosis, rheumatoid arthritis, stroke, hyperlipidemia, hypertriglycemia, hyperglycemia, hyperlipoproteinemia, substance abuse, drug overdose, compulsive behavior disorders (such as paw licking in dog), and addictive behaviors such as for example, gambling, and alcoholism, comprising administering a therapeutically effective amount of a compound of formula I or a pharmaceutically acceptable salt, solvate, enantiomer, racemate, diastereomer or mixture thereof.

The present invention provides a compound of formula (I) useful for the manufacture of a medicament for the treatment, prevention and/or amelioration of symptoms associated with obesity and Related Diseases.

In another embodiment, the present invention provides a compound of formula I or a pharmaceutically acceptable salt, solvate, enantiomer, racemate, diastereomer or mixture thereof, useful as an appetite suppressant.

The present invention provides a method of achieving weight loss while maintaining or minimizing the loss of lean muscle mass.

DETAILED DESCRIPTION OF THE INVENTION

As used herein, the term "patient" includes human and non-human animals such as companion animals (dogs and cats and the like) and livestock animals.

The preferred subject of treatment, amelioration and/or prevention of obesity and Related Diseases is a human.

The terms "treating" and "treat", as used herein, include their generally accepted meanings, i.e., preventing, prohibiting, restraining, alleviating, ameliorating, slowing, stopping, or reversing the progression or severity of a pathological condition, of sequela thereof, described herein.

The terms "ameliorating" "preventing", "prevention of", "prophylaxis", "prophylactic" and "prevent" are used herein interchangeably and refer to reducing the severity of the symptoms associated with obesity and Related Diseases in a patient afflicted with same or reducing the likelihood that the recipient of a compound of formula I will incur or develop any of the pathological conditions, or sequela thereof, described herein.

As used herein, the term "effective amount" is synonymous with "effective dose" and means an amount of a compound of formula I that is sufficient in one or more administrations for preventing, ameliorating or treating a condition, or detrimental effects thereof, herein described, or an amount of a compound of formula I that is sufficient for antagonizing the opioid receptors to achieve the objectives of the invention.

The term "pharmaceutically acceptable" is used herein as an adjective and means substantially non-deleterious to the recipient patient.

The term "Active Ingredient" as used herein means a compound of formula I or a combination of compounds of formula I or a combination of a compound of formula I and a co-antagonist of the opioid receptor.

The term "formulation", as in pharmaceutical formulation, or "pharmaceutical composition" is intended to encompass a product comprising the active ingredient (compound of formula I), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical formulations of the present invention encompass any effective composition made by admixing a compound of the present invention and a pharmaceutical carrier. The pharmaceutical formulations of the present invention also encompass a compound of the formula I and a pharmaceutically acceptable co-antagonist of opioid receptors useful for the treatment and/or prevention of obesity or Related Diseases. Accordingly a pharmaceutical formulation of a compound of formula I includes a pro-drug formed in-vivo upon administration of a compound of formula I to a patient in need thereof.

The term "co-antagonist" of the opioid re eptor as used herein, represents a compound which is known to be therapeutically effective in the treatment and/or prevention of obesity The term "Related Diseases" as used herein refers to such symptoms, diseases or conditions caused by, exacerbated by, induced by or adjunct to the condition of being obese. Such diseases, conditions and/or symptoms include but are not limited to eating disorders (bulimia, anorexia nervosa, etc.), diabetes, diabetic complications, diabetic retinopathy, sexual/reproductive disorders, depression (particularly that induced by the awareness and loss of self esteem associated with obesity), anxiety, epileptic seizure, hypertension, cerebral hemorrhage, congestive heart failure, sleeping disorders, atherosclerosis, rheumatoid arthritis, stroke, hyperlipidemia, hypertriglycemia, hyperglycemia, and hyperlipoproteinemia.

The term "suitable solvent" refers to any solvent, or mixture of solvents, inert to the ongoing reaction that sufficiently solubilizes the reactants to afford a medium within which to effect the desired reaction.

The term "mutual solvent" means a solvent that is used to dissolve sufficiently, two or more components of a reaction or mixture separately prior to reaction or mixing, that is a solvent common to more than one reagents or components of a mixture.

The term "nitrogen containing heterocycle" refers to a monocycle which is a 4, 5, 6, or 7-member ring containing 1, 2 or 3 nitrogen atoms in addition to the carbon atoms completing the ring size, or a combination of 1 nitrogen atom and 1, or 2 atoms selected from oxygen, and sulfur in addition to the appropriate number of carbon atoms completing the ring size. A nitrogen containing heterocycle as used here may have 0, 1 or 2 double bonds.

The term $C_1$-$C_8$ alkyl refers to and includes all groups, structural isomers and/or homologues of alkyl groups having from 1 to 8 carbon atoms. When the term $C_1$-$C_8$ alkyl precedes or prefixes another group, the term $C_1$-$C_8$ alkyl, only limits the number of carbon atoms in the alkyl component. For example $C_1$-$C_8$ alkylaryl, means an aryl group having a $C_1$-$C_8$ alkyl group substituent such that the number of carbon atoms in the group $C_1$-$C_8$ alkylaryl is effectively the number of carbon atoms in the aryl group plus the number of carbon atoms in the $C_1$-$C_8$ alkyl group. Similarly, the term $C_1$-$C_8$ alkylcycloalkane, refers to a cycloalkane group having a $C_1$-$C_8$ alkylsubstituent, and wherein the entire group $C_1$-$C_8$ alkylcycloalkane may itself be a substituent attached at either the alkyl group or the cycloalkyl group to a susbtrate.

The term "cycloalkane" means cycloalkanes having from 3 to 8 carbon atoms i.e. from cyclopropane to cyclooctane unless otherwise indicated. Accordingly, the term $C_3$-$C_8$ cycloalkane referes to cycloalkanes ranging from cyclopropyl to cycloctyl inclusive.

The term "halo" as used herein refers to a halogen including fluorine, chlorine, bromine or iodine.

As used herein the terms "alkenyl" refers to straight or branched carbon atoms having 1 or 2 carbon-carbon double bonds.

As used herein the terms "alkynyl" refers to straight or branched carbon atoms having 1 or 2 carbon-carbon triple bonds.

As used herein the term "alkoxy" refers to the group "O-alkyl" wherein alkyl is as indicated for the specific situation or as defined previously.

The term "aryl" as used herein refers to compounds or groups having the Hückel 4n+2 pi electron arrangement and includes phenyl benzyl, naphthyl, but excludes carbazoles.

As used herein, the term "protecting group" refers to a group useful for masking reactive sites in a molecule to enhance the reactivity of another group or allow reaction at another desired site or sites following which the protecting group may be removed. Protecting groups are usually used to protect or mask groups including but not limited to —OH, —NH, and —COOH. Suitable protecting groups are known to one of skill in the art and are described in Protecting groups in Organic Synthesis, 3$^{rd}$ edition, Greene, T. W.; Wuts, P. G. M. Eds., John Wiley and Sons, New York 1999.

As used herein, the term "solvate" is a form of the compound of the invention wherein a crystal or crystals of a compound of the invention have been formed from a stoichiometric or non-stoichiometric amount of the compound of formula I and a solvent. Typical solvating solvents include for example, water, methanol, ethanol, acetone and dimethylformamide.

In those instances where a compound of the invention possesses acidic or basic functional groups, various salts may be formed which are more water soluble and/or more physiologically suitable than the parent compound. Representative pharmaceutically acceptable salts, include but are not limited to, the alkali and alkaline earth salts such as lithium, sodium, potassium, calcium, magnesium, aluminum and the like. Salts are conveniently prepared from the free acid by treating the acid in solution with a base or by exposing the acid to an ion-exchange resin.

Included within the definition of pharmaceutically acceptable salts are the relatively non-toxic, inorganic and organic base addition salts of compounds of the present invention, for example, ammonium, quaternary ammonium, and amine cations, derived from nitrogenous bases of sufficient basicity to form salts with the compounds of this invention (see, for example, S. M. Berge, et al., "Pharmaceutical Salts," *J. Phar. Sci.*, 66: 1-19 (1977)). Moreover, the basic group(s) of the compound of the invention may be reacted with suitable organic or inorganic acids to form salts such as acetate, benzenesulfonate, benzoate, bicarbonate, bisulfate, bitartrate, borate, hydrobromide, camsylate, carbonate, clavulanate, citrate, chloride, edetate, edisylate, estolate, esylate, fluoride; fumarate, gluceptate, gluconate, glutamate, glycolylarsanilate, hexylresorcinate, hydrochloride, hydroxynaphthoate, hydroiodide, isothionate, lactate, lactobionate, laurate, malate, malseate, mandelate, mesylate, methylbromide, methylnitrate, methylsulfate, mucate, napsylate, nitrate, oleate, oxalate, palmitate, pantothenate, phosphate, polygalacturonate, salicylate, stearate, subacetate, succinate, tannate, tartrate, tosylate, trifluoroacetate, trifluoromethane sulfonate, and valerate.

A compound of the invention as illustrated by formula I may occur as any one of its positional isomers, stereochemical isomers or regioisomers, all of which are objects of the invention. Certain compounds of the invention may possess one or more chiral centers, and thus, may exist in optically active forms. Likewise, when the compounds contain an alkenyl or alkenylene group, there exists the possibility of cis- and trans-isomeric forms of the compounds. The R- and S-isomers and mixtures thereof, including racemic mixtures as well as mixtures of enantiomers or cis- and trans-isomers, are contemplated by this invention. Additional asymmetric carbon atoms can be present in a substituent group such as an alkyl group. All such isomers as well as the mixtures thereof are intended to be included in the invention. If a particular stereoisomer is desired, it can be prepared by methods known in the art by using stereospecific reactions with starting materials which contain the asymmetric centers and are already resolved or, alternatively by methods which lead to mixtures of the stereoisomers and subsequent resolution by known methods. For example, a racemic mixture may be reacted with a single enantiomer of some other compound i.e. a chiral resolving agent. This changes the racemic form into a mixture of stereoisomers and diastereomers, because they have different melting points, different boiling points, and different solubilities and can be separated by conventional means, such as, for example, crystallization or chromatography.

The compound(s) of the present invention have shown anorexigenic effects, and are thus useful as appetite suppressants either as a single therapy or in conjunction with exercise and/or other effective appetite suppressing or weight loss medications.

The efficacy of the compounds of the present invention have been shown by their activity in several models including an SPA, and GTP-gamma S binding assays, and an opioid receptor ex-vivo binding assay.

PREFERRED EMBODIMENTS OF THE INVENTION

A compound of formula I preferably exists as the free base or a pharmaceutically acceptable salt. More preferred is the pharmaceutically acceptable salt, wherein the salt is the hydrochloride salt, the bisulfate salt, mesylate or the oxalic acid salt of the compound of formula I.

Preferred embodiments of the compound of formula I include the substructures Ia, Ib, and Ic as shown below:

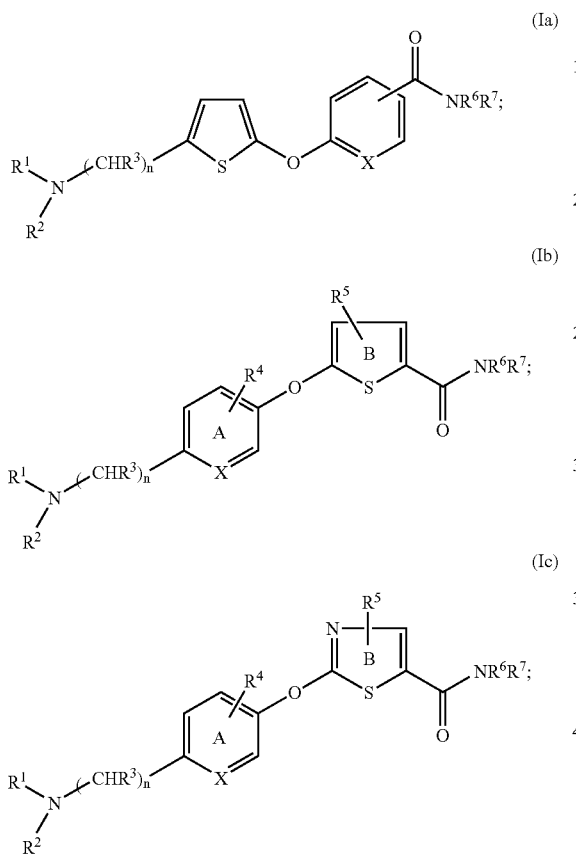

For the groups $R^1$ and $R^2$

Preferred $R^1$ and $R^2$ groups are independently selected from the group consisting of hydrogen, methyl, ethyl, propyl, pentyl, and isopropyl. Also preferred are $R^1$ and $R^2$ groups independently selected from the group consisting of hydrogen, methyl, ethyl, propyl, isopropyl, phenyl,

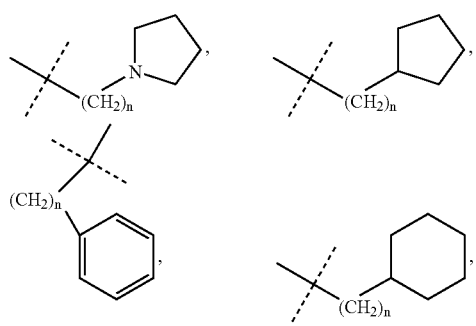

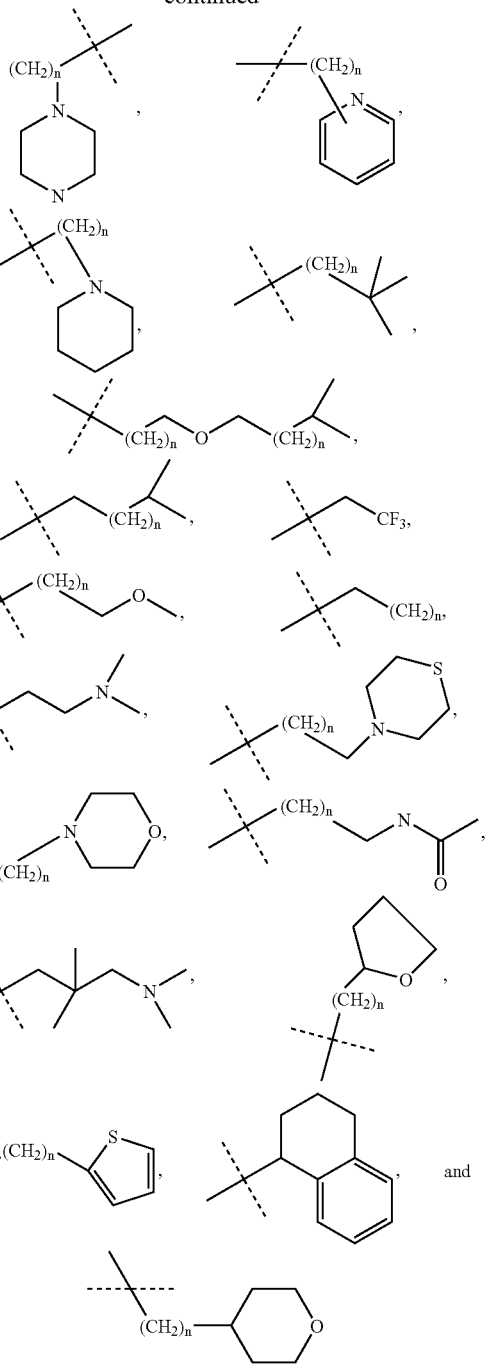

each of which is optionally substituted with a group selected from the group consisting of halogen, $C_1$-$C_8$ alkyl, $C_1$-$C_8$ haloalkyl, $C_1$-$C_8$ thioalkyl, $C_1$-$C_8$ alkylamino, phenyl, $C_1$-$C_8$ alkylsubstituted phenyl, $C_4$-$C_8$ heterocycle or $C_1$-$C_4$ alkyl heterocycle; or combine with a group selected from $C_1$-$C_8$ alkyl, halogen, $C_1$-$C_8$ haloalkyl, $C_1$-$C_8$ thioalkyl, $C_1$-$C_8$ alkylamino, phenyl, $C_1$-$C_8$ alkylsubstituted phenyl, $C_4$-$C_8$ heterocycle or $C_1$-$C_4$ alkyl heterocycle to form a substituted or unsubstituted bicycle.

Also preferred are $R^1$ and $R^2$ groups which combine with each other or with 1 or 2 atoms adjacent to the nitrogen atom to form a group selected from the group consisting of hydrogen, methyl, ethyl, propyl, pentyl, and isopropyl,

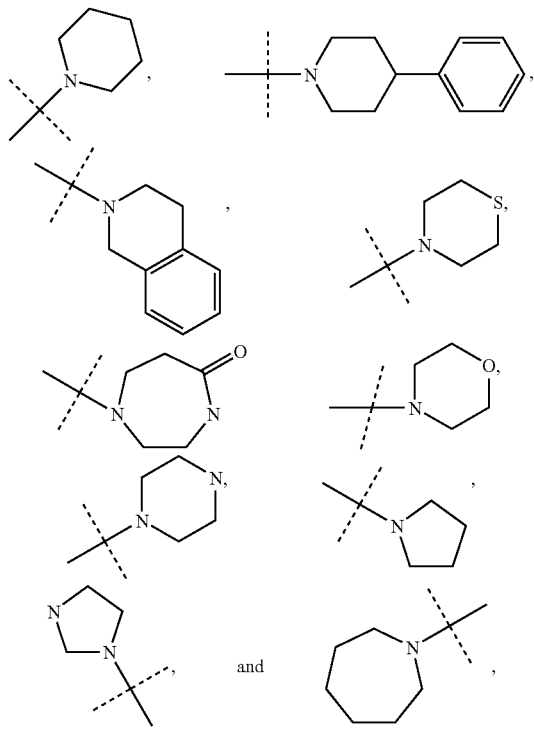

each of which is optionally substituted with a group selected from the group consisting of halogen, $C_1$-$C_8$ alkyl, $C_1$-$C_8$ haloalkyl, $C_1$-$C_8$ thioalkyl, $C_1$-$C_8$ alkylamino, phenyl, $C_1$-$C_8$ alkylsubstituted phenyl, $C_4$-$C_8$ heterocycle or $C_1$-$C_4$ alkylheterocycle.

Preferred $R^3$ and $R^{3'}$ Groups

A preferred $R^3$ is hydrogen. A preferred $R^{3'}$ group is selected from hydrogen, methyl, ethyl, propyl, isopropyl, phenyl and benzyl.

Preferred $R^4$ Groups

A preferred $R^4$ group is selected from the group consisting of hydrogen, halo, $C_1$-$C_5$ alkyl, $C_1$-$C_5$ haloalkyl, $C_1$-$C_5$ alkoxy, $C_1$-$C_5$ alkylamino, phenyl, $C_1$-$C_5$ alkylphenyl, C1-C5 alkylcycloalkyl, and $C_1$-$C_5$ thioalkyl. More preferred is a $R^4$ group selected from the group consisting of hydrogen, methyl, ethyl, isopropyl, bromo, chloro, fluoro, trifluoromethyl, methoxy, ethoxy, thiomethyl, phenyl, and benzyl. A most preferred $R^4$ group is selected from the group consisting of hydrogen, methyl, ethyl, isopropyl, fluoro, chloro, bromo, trifluoromethyl, methoxy, ethoxy, propoxy, isopropoxy, and benzyl.

Though the groups $R^4$ and $R^5$ may exist as multiple substituents on their respective ring substrates, a preferred embodiment of the invention involves compounds wherein each of $R^4$, and $R^5$ when present are singly or doubly substituted on their respective ring substrates.

Preferred $R^5$ Groups

A preferred $R^5$ group is selected from the group consisting of hydrogen, halo, $C_1$-$C_5$ alkyl, $C_1$-$C_5$ haloalkyl, $C_1$-$C_5$ alkoxy, $C_1$-$C_5$ alkylamino, phenyl, $C_1$-$C_5$ alkylphenyl, $C_1$-$C_5$ alkylcycloalkyl, and $C_1$-$C_5$ thioalkyl. More preferred is an $R^5$ group selected from the group consisting of hydrogen, methyl, ethyl, isopropyl, bromo, chloro, fluoro, trifluoromethyl, methoxy, ethoxy, thiomethyl, phenyl, and benzyl. A most preferred $R^5$ group is selected from the group consisting of hydrogen, methyl, ethyl, isopopropyl, fluoro, bromo, chloro, trifluoromethyl, methoxy, ethoxy, trifluoromethoxy, and benzyl.

Preferred $R^6$ and $R^7$ Groups

Preferred are $R^6$ and $R^7$ groups independently selected from the group consisting of hydrogen, methyl, ethyl, propyl, pentyl, isopropyl, phenyl and benzyl. Most preferred $R^6$ and $R^7$ are hydrogen atoms.

Preferred E Group

A most preferred E group is an oxygen atom (O).

Preferred A-ring

A preferred A-ring is a phenyl, thiophene, pyridyl, thiazole, imidazole, imidazoline, pyrazole, oxazole, or isothiazole, provided that both A and B rings are not each 5 or 6-member rings.

Preferred B-ring

A preferred B-ring is a phenyl, pyridyl, thiophene, imidazole, imidazoline, pyrazole, oxazole, isothiazole, or a thiazole ring.

Preferred Values for n and m

A preferred value for n is 0, 1, or 2.
A preferred value for m is 1 or 2 or 3.
A preferred value for y or z is 0 or 1.
A preferred value for p is 0 or 1.
A preferred value for k is 0 or 1.
A preferred value for j is 0 or 1 provided that k and j are not simultaneously equal to 1.

A preferred compound is a compound selected from the group consisting of:

5-{4-[(3-Methyl-butylamino)-methyl]-phenoxy}-thiophene-2-carboxamide

5-{4-[(3,3-Dimethyl-butylamino)-methyl]-phenoxy}-thiophene-2-carboxamide,

5-{4-[(2-Cyclopentyl-ethylamino)-methyl]-phenoxy}-thiophene-2-carboxamide,

5-{4-[(3-Ethyl-pentylamino)-methyl]-phenoxy}-thiophene-2-carboxamide,

5-{4-[(Cyclohexylmethyl-amino)-methyl]-phenoxy}-thiophene-2-carboxamide, 5-(4-{[2-(4-Fluoro-phenyl)-ethylamino]-methyl}-phenoxy)-thiophene-2-carboxamide, 5-{2-Chloro-4-[(3-methyl-butylamino)-methyl]-phenoxy}-thiophene-2-carboxamide, 5-{2-Chloro-4-[(3,3-dimethyl-butylamino)-methyl]-phenoxy}-thiophene-2-carboxamide, 5-(2-Chloro-4-{[2-(4-fluoro-phenyl)-ethylamino]-methyl}-phenoxy)-thiophene-2-carboxamide, 5-{2-Fluoro-4-[(3-methyl-butylamino)-methyl]-phenoxy}-thiophene-2-carboxamide, 5-{4-[(3,3-Dimethyl-butylamino)-methyl]-2-fluoro-phenoxy}-thiophene-2-carboxamide, 5-(2-Fluoro-4-{[2-(4-fluoro-phenyl)-ethylamino]-methyl}-phenoxy)-thiophene-2-carboxamide, 5-{2-Methoxy-4-[(3-methyl-butylamino)-methyl]-phenoxy}-thiophene-2-carboxamide, 5-(4-{[2-(4-Fluoro-phenyl)-ethylamino]-methyl}-2-methoxy-phenoxy)-thiophene-2-carboxamide, 4-{5-[(3-Methyl-butylamino)-methyl]-thiazol-2-yloxy}-benzamide, 3-Methoxy-4-{5-[(3-methyl-butylamino)-methyl]-thiazol-2-yloxy}-benzamide, 4-{5-[(3,3-Dimethyl-butylamino)-methyl]-thiazol-2-yloxy}-benzamide,
4-(5-{[2-(4-Fluoro-phenyl)-ethylamino]-methyl}-thiazol-2-yloxy)-benzamide,
4-(5-{[2-(4-Fluoro-phenyl)-ethylamino]-methyl}-thiazol-2-yloxy)-3-methoxy-benzamide,
4-{5-[(Cyclohexylmethyl-amino)-methyl]-thiazol-2-yloxy}-benzamide,
2-(4-Pentylaminomethyl-phenoxy)-thiazole-5-carboxamide,
2-{4-[(3-Methyl-butylamino)-methyl]-phenoxy}-thiazole-5-carboxamide,
2-{4-[(3,3-Dimethyl-butylamino)-methyl]-phenoxy}-thiazole-5-carboxamide,
2-(4-{[2-(4-Fluoro-phenyl)-ethylamino]-methyl}-phenoxy)-thiazole-5-carboxamide,
2-{2-Chloro-4-[(3-methyl-butylamino)-methyl]-phenoxy}-thiazole-5-carboxamide,
2-{2-Fluoro-4-[(3-methyl-butylamino)-methyl]-phenoxy}-thiazole-5-carboxamide,
2-{2-Methyl-4-[(3-methyl-butylamino)-methyl]-phenoxy}-thiazole-5-carboxamide,
2-{2-Methoxy-4-[(3-methyl-butylamino)-methyl]-phenoxy}-thiazole-5-carboxamide,
4-[5-(2,6-Dimethyl-morpholin-4-ylmethyl)-thiazol-2-yloxy]-benzamide,
4-{5-[(3-Methoxy-propylamino)-methyl]-thiazol-2-yloxy}-benzamide,
4-{4-Chloro-5-[(3-methyl-butylamino)-methyl]-thiazol-2-yloxy}-benzamide,
4-(5-Butylaminomethyl-4-chloro-thiazol-2-yloxy)-benzamide,
4-{4-Chloro-5-[(3,3-dimethyl-butylamino)-methyl]-thiazol-2-yloxy}-benzamide,
4-[5-(Phenethylamino-methyl)-thiophen-2-yloxy]-benzamide,
4-{5-[(3-Methyl-butylamino)-methyl]-thiophen-2-yloxy}-benzamide,
4-(5-{[2-(3-Fluoro-phenyl)-ethylamino]-methyl}-thiophen-2-yloxy)-benzamide,
4-{5-[(2-Cyclopentyl-ethylamino)-methyl]-thiophen-2-yloxy}-benzamide,
4-{5-[(2-Thiophen-2-yl-ethylamino)-methyl]-thiophen-2-yloxy}-benzamide,
4-{5-[(3,3-Dimethyl-butylamino)-methyl]-thiophen-2-yloxy}-benzamide,
3-Methoxy-4-[5-(phenethylamino-methyl)-thiophen-2-yloxy]-benzamide hydrochloride,
3-Methoxy-4-{5-[(3-methyl-butylamino)-methyl]-thiophen-2-yloxy}-benzamide hydrochloride,
4-[5-(2-Phenethylamino-ethyl)-thiophen-2-yloxy]-benzamide hydrochloride, or a pharmaceutically acceptable salt, solvate, enantiomer, diastereomer and diastereomric mixture thereof.

A more preferred compound of the invention is a compound selected from the group consisting of:
4-[5-(Phenethylamino-methyl)-thiophen-2-yloxy]-benzamide

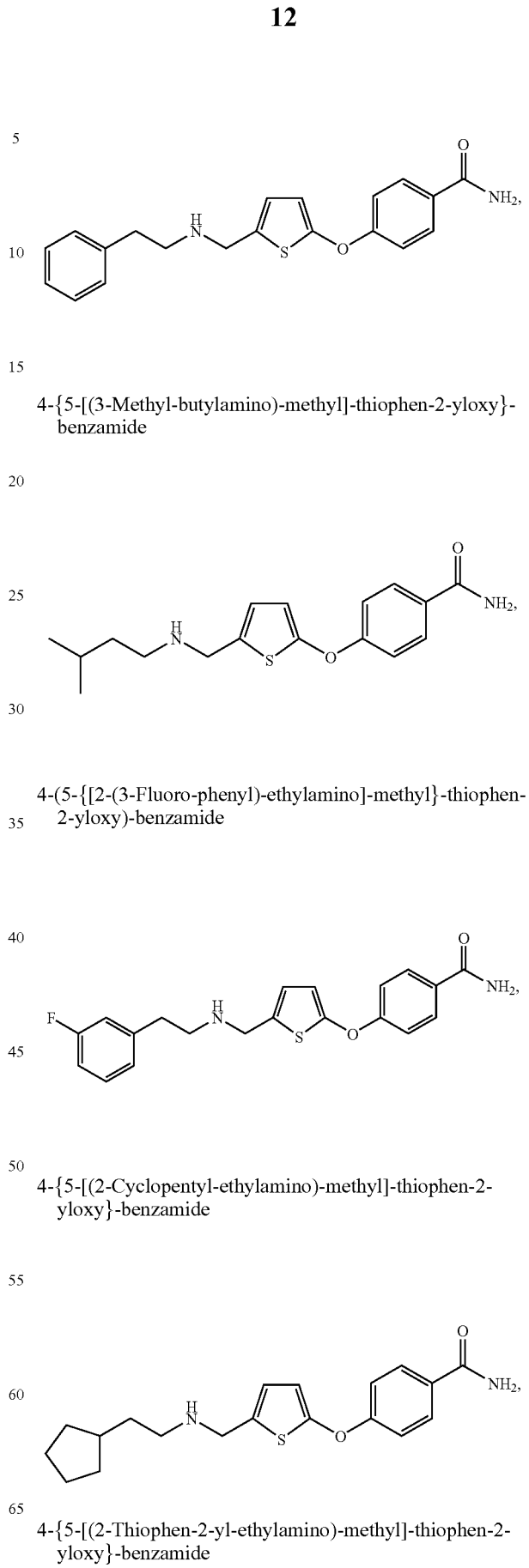

4-{5-[(3-Methyl-butylamino)-methyl]-thiophen-2-yloxy}-benzamide 4-(5-{[2-(3-Fluoro-phenyl)-ethylamino]-methyl}-thiophen-2-yloxy)-benzamide 4-{5-[(2-Cyclopentyl-ethylamino)-methyl]-thiophen-2-yloxy}-benzamide 4-{5-[(2-Thiophen-2-yl-ethylamino)-methyl]-thiophen-2-yloxy}-benzamide

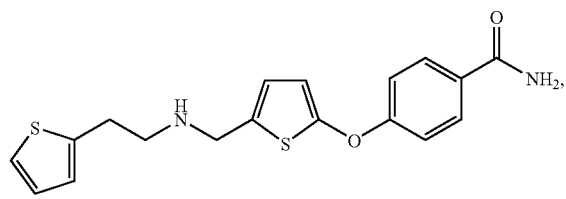

4-{5-[(3,3-Dimethyl-butylamino)-methyl]-thiophen-2-yloxy}-benzamide

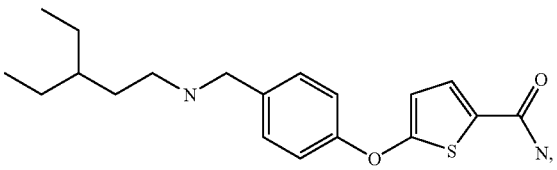

2-{4-[(3-Methylbutylamino)methyl]phenoxy}thiazole-5-carboxamide

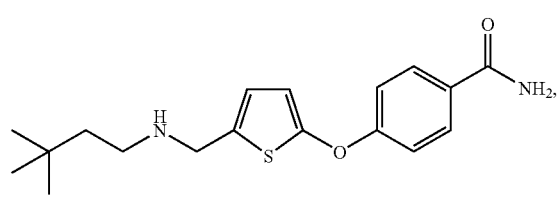

3-Methoxy-4-[5-(phenethylamino-methyl)-thiophen-2-yloxy]-benzamide hydrochloride

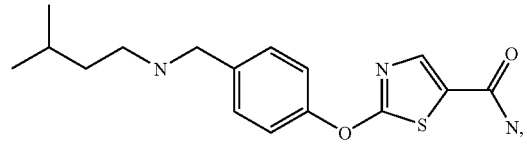

2-(4-{[2-(Tetrahydropyran-4-yl)ethylamino]methyl}phenoxy)thiazole-5-carboxamide methanesulfonate

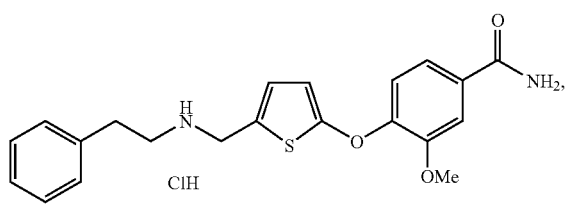

3-Methoxy-4-{5-[(3-methyl-butylamino)-methyl]-thiophen-2-yloxy}-benzamide hydrochloride

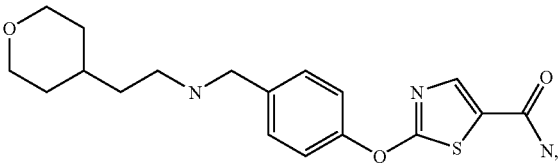
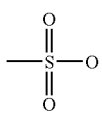

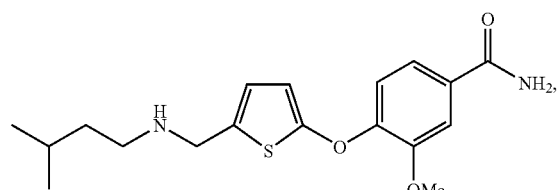

4-[5-(2-Phenethylamino-ethyl)-thiophen-2-yloxy]-benzamide hydrochloride

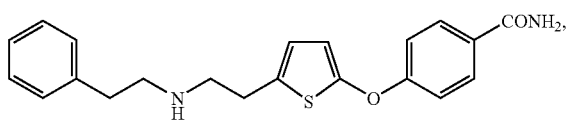

5-{4-[(3-Ethylpentylamino)methyl]phenoxy}thiophene-2-carboxamide and a pharmaceutically acceptable salt, solvate, enantiomer, diastereomer or diastereomeric mixture thereof.

Making Compounds of the Invention

In a typical protocol, an optionally substituted carbaldehyde, e.g., the thiophene carbaldehyde, 5-bromo-thiophene-2-carbaldehyde (1) where X is bromo or synthon thereof, is employed.

Scheme 1

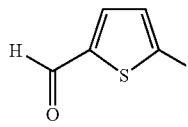

1

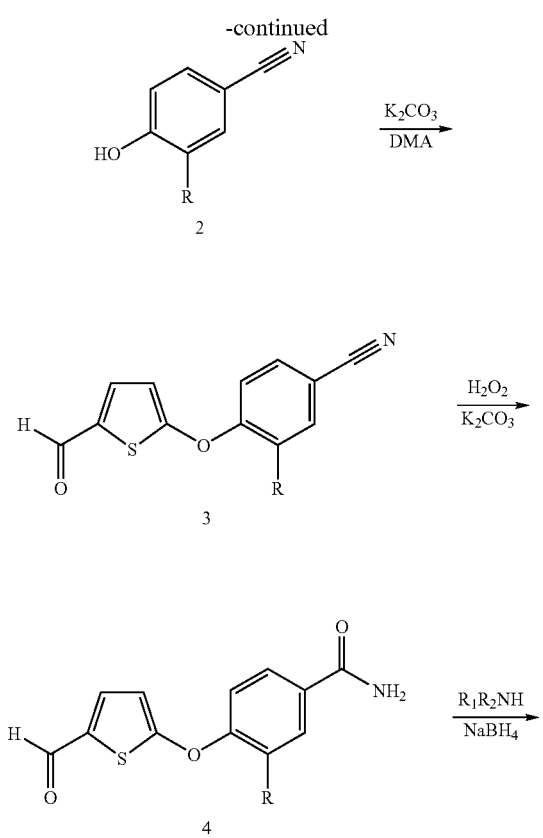

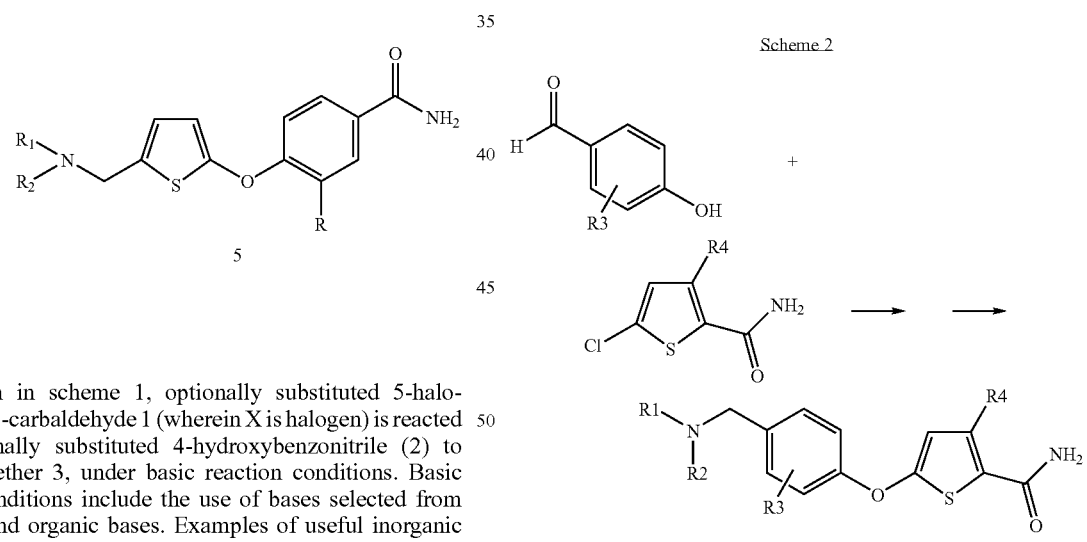

80-100° C. Certain reactions may require refluxing conditions while others may require lower temperatures depending on the particular substrates.

The nitrile compound 3 is converted to the carboxamide 4 by hydrolysis procedures known to one of skill in the art. For example, the compound 3 is reacted with potassium carbonate or other suitable base in the presence of hydrogen peroxide in a suitable organic solvent i.e. DMSO or DMF. The resulting amide compound 4 is reductively aminated with a suitably substituted amine. The reductive amination may be performed in two steps or a single step depending on the stability of the intermediate imine. Typically, the compound 4 is reacted with a primary or secondary amine in methanol as solvent. Molecular sieves may be added to enhance the efficiency of the amination reaction. In a second step, the reducing agent, typically, sodium borohydride or other hydride reducing agent is added to the reaction mixture. The progress of the reaction may be monitored by TLC, HPLC, HPLC-MS or other analytical technique known to one of skill in the art to determine the substantial completion of each step and timing for the addition of the next reagent. The reductive amination of compound 4 results in the compound of formula 5, which is itself a compound of the invention. Analogues of compounds 3 and 5 having one or more substituent R groups may be prepared by using appropriately substituted starting materials or by inter-conversion of substituent functionality, that is, converting a substituent amenable to intermediate reactions i.e. converting a protected group or synthon to the desired substituent in a later step.

An alternate protocol illustrated by Scheme 2 is the use of the carboxamide starting material to prepare, for example, compounds wherein the B-ring is a thiophenyl ring or similar five-member heterocyclic ring.

A shown in scheme 1, optionally substituted 5-halothiophene-2-carbaldehyde 1 (wherein X is halogen) is reacted with optionally substituted 4-hydroxybenzonitrile (2) to afford the ether 3, under basic reaction conditions. Basic reaction conditions include the use of bases selected from inorganic and organic bases. Examples of useful inorganic bases include but are not limited to potassium carbonate, sodium carbonate, sodium hydroxide, potassium hydroxide, calcium carbonate, and cesium carbonate. Examples of organic bases include but are not limited to potassium hexamethyl disilazide, n-butyl lithium, sodium hydride, hexamethylphosphorous triamide, (HMPT), and the like. The basic conditions are complemented by the presence of a solvent, preferably an organic solvent. Preferred organic solvents include protic solvents or polar aprotic solvents. Most preferred solvents include DMA (dimethylacetamide) dimethylformamide, methanol, dimethylsulfoxide. A most preferred basic reaction condition involves the use of potassium carbonate in dimethylacetamide at temperatures from about The use of the carboxamide starting material is particularly preferred for compounds of the invention where the B-ring is thiophenyl, or thiazolyl group. The carboxamide may be introduced as part of the starting material where the appropriate surrogate for the B-ring is commercially available, or may be prepared by known procedures or known modifications thereof. The initially formed ether is reductively aminated at the aldehyde functionality to afford the amine product (Scheme 2).

A modified protocol is provided in Scheme 3 wherein the nucleophilic displacement reaction to form the ether linkage is performed after installation of the amino sidechain.

Scheme 3

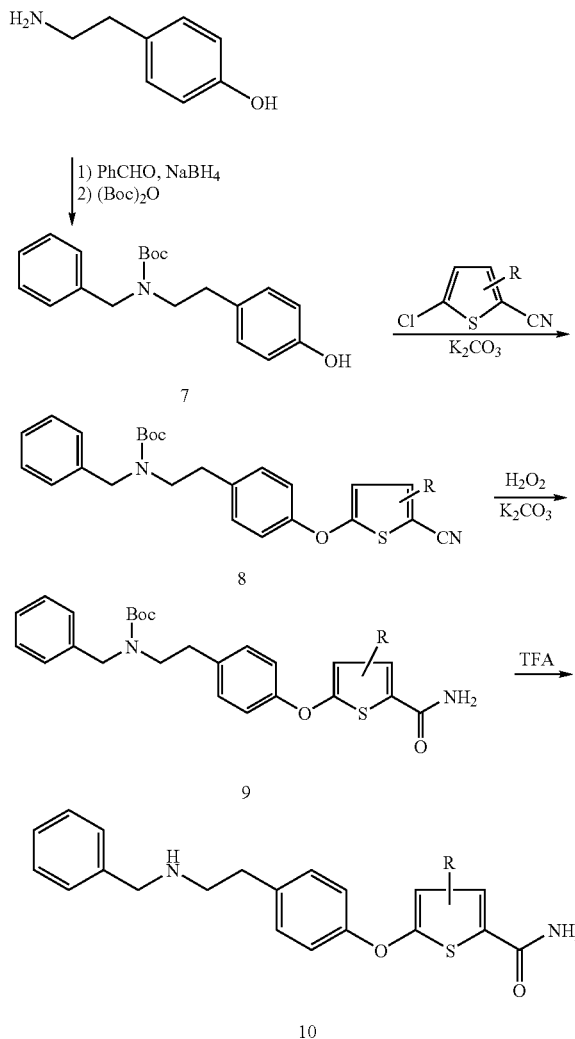

instance by carbonyl elongation reactions. An example is a modified Wittig type reaction as shown in Scheme 4.

Scheme 4

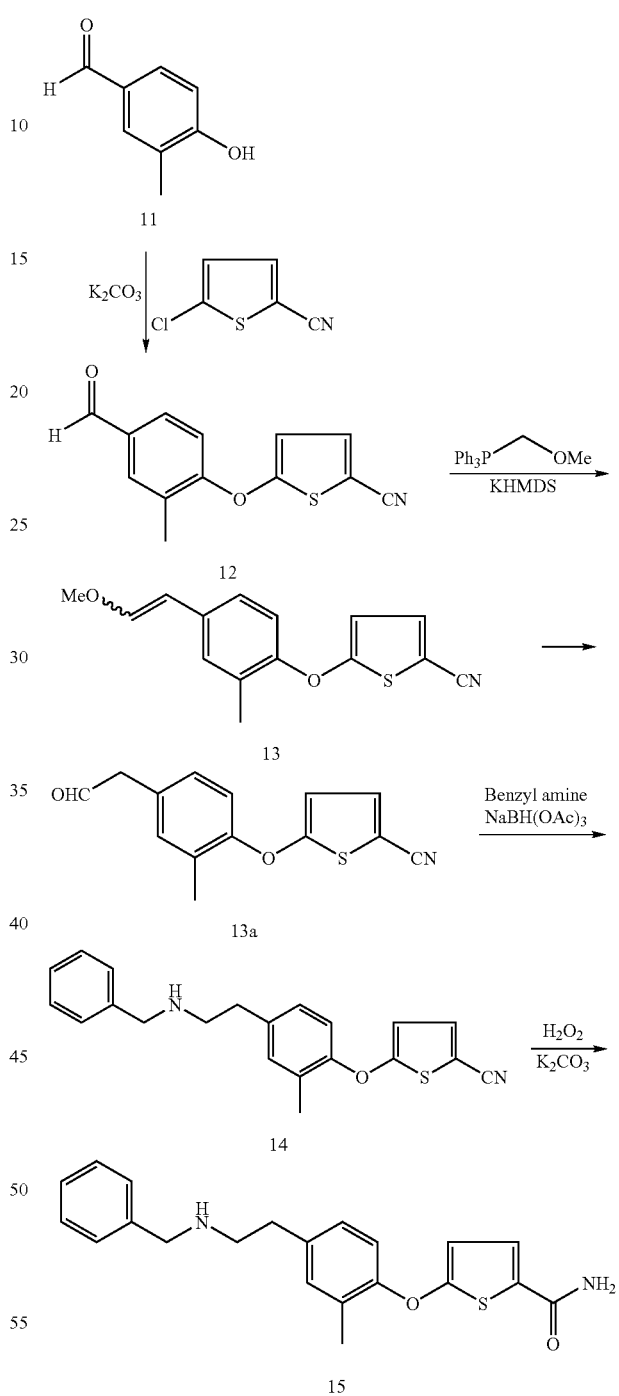

Under this protocol an appropriately substituted aminophenol is reductively aminated with an optionally substituted benzaldehyde. The reductive amination is accomplished in the presence of sodium borohydride or other reducing agent and a suitable base. Tertiary-butoxycarbonyl anhydride (Boc-anhydride) is used to afford protection of the incipient free amine as the Boc-protected amine. The resulting phenoxy compound 7 is then reacted with a B ring source such as for example, an appropriately substituted or unsubstituted halogeno thiophenyl nitrile or carboxamide or synthon thereof. The coupling of the B and A-ring sources is performed under basic conditions to afford the ether 8 for the above example. In the next step, the nitrile group, if present as in the current example, is hydrolyzed to the carboxamide as discussed previously. The protecting group may be removed by use of trifluoroacetic acid or hydrochloric acid using procedures known to one of skill in the art. One of skill in the art is aware that appropriately substituted analogs of the compound 10 may be prepared by starting with appropriately substituted starting materials or surrogates thereof which may be converted to the desired substituents.

Compounds of formula I having varying alkyl chain lengths on the amino side chain may be prepared in one The protocol of Scheme 4 and known variations thereof, allow manipulation of the amino side chain for chain length and/or substituents. Under this protocol, optionally substituted 4-hydroxybenzaldehyde e.g. compound 11 is reacted with an optionally substituted 5-membered ring nitrile compound having a suitable leaving group, e.g. 5-chloro-2-cyanothiophene. The product 12 or analog thereof, is then subjected to a carbonyl elongation reaction such as, for example, the Wittig reaction and variations thereof. (see Organophosporus agents in organic Synthesis, J. I. G. Cadogan, Ed., Academic Press London (1979); see also, J. March, Advanced Organic Chemistry, 3$^{rd}$ Edition, Wiley Interscience, New York N.Y., (1995). In the example given, the aldehyde 12 is reacted with methoxymethyltriphenylphosphonium chloride (available from Aldrich chemical Company, Milwaukee, USA) using a strong base such as, for example, KHMDS (potassium hexamethyl disilizade), n-butyl lithium, sec-butyl lithium and the like, to generate the incipient carbanion. The resulting vinylmethyl ether 13 is hydrolyzed using a strong acid, e.g., p-toluenesulfonic acid, HCl or sulfuric acid to generate the new aldehyde 13a. The aldehyde 13a is then reacted with a suitable amine followed by reduction to afford the reductive amination product 14. Details of each step in the schemes disclosed herein are provided in the experimental section, or may be found in reference organic synthesis texts or are known to one of skill in the art. Some reactions such as the formation of the ylide specie for the Wittig and related reactions perform better at reduced temperatures ranging from about −10° C. to about −80° C. Other reactions perform better at elevated temperatures ranging from about 30° C. to about 150° C., and yet other reactions perform better at ambient temperature ranging from about 15° C. to about 30° C.

Compounds of the invention wherein the groups R$^1$ and R$^2$ combine with each other and with the nitrogen atom to which they are attached to form a nitrogen containing heterocycle, may be prepared, for example, according to scheme 5.

According to Scheme 5, the reductive amination of aldehyde with amine is performed using a cyclic amine having the desired ring size and/or substituents. For example, the reaction of an optionally substituted cyclic amine i.e. optionally substituted pyrrolidine (shown) with the aldehyde 4 results in the formation of compound 17 wherein R$^1$ and R$^2$ combine to form the nitrogen containing heterocyclic amine. The starting material 2-chloro-5-cyanothiophene 16 may be prepared from the corresponding carboxamide (2-carboxamido-5-chlorothiophene), which in turn may be prepared from the corresponding carboxylic acid analog, i.e. 5-chlorothiophene-2-carboxylic acid. Procedures for converting the carboxylic acid derivative to the carboxamide followed by dehydration to form the nitrile 16 are known to one of skill in the art, are disclosed in general organic reference texts, or are disclosed partially or in total in the experimental section herein.

Similarly, compounds of formula I having 5-member heterocyclic rings other than thiophene, may be prepared as shown in Scheme 6 (for thiazole compounds) by using other appropriately substituted 5-member ring reagents.

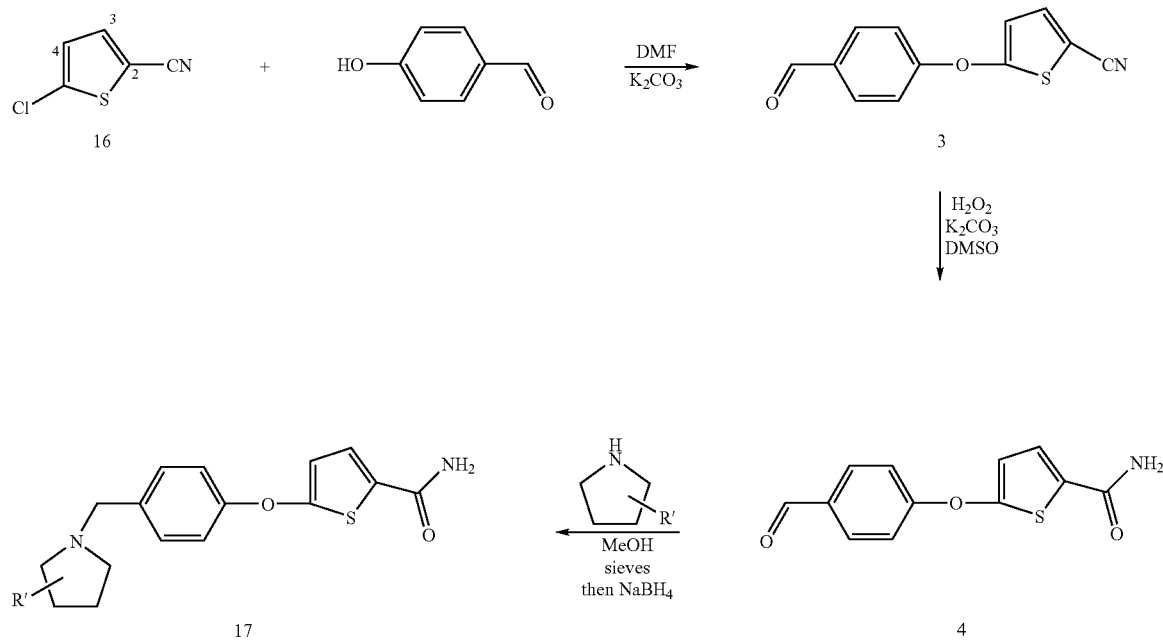

Scheme 6

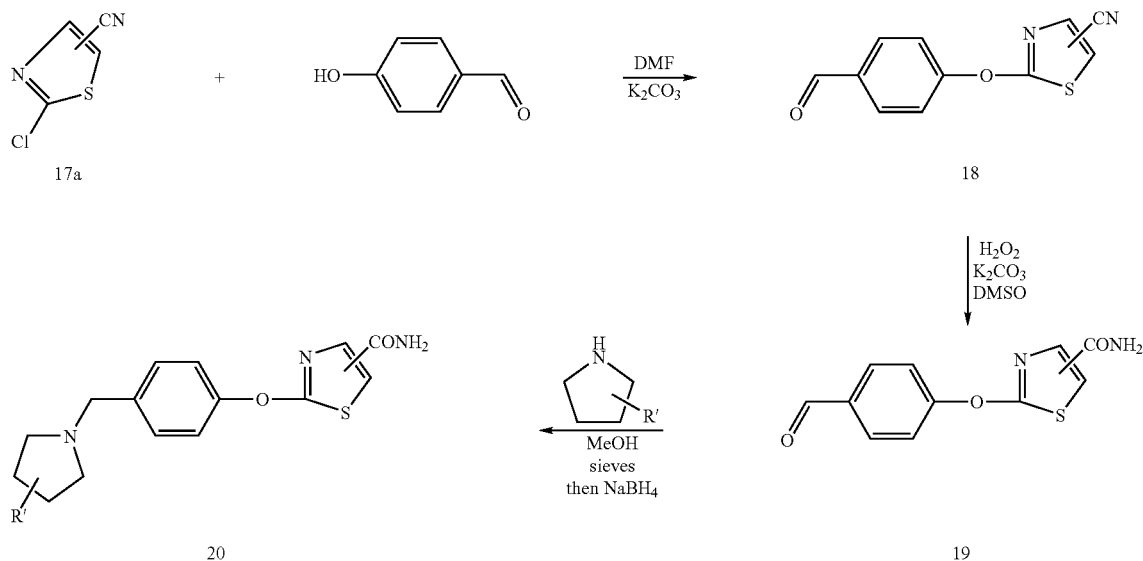

As shown above, nucleophilic displacement reaction of appropriately substituted 2-halothiazole compound 17a on an optionally substituted hydroxy benzaldehyde affords the ether 18. The cyano group of the ether 18 is then hydrolyzed under basic conditions such as in the presence of potassium carbonate and hydrogen peroxide as promoter to afford the carboxamide 19. The carboxamide 19 is reductively aminated to the amine 20. The hydroxy benzaldehyde compound or optionally substituted analogs or positional isomers thereof may be obtained from commercial sources or may be prepared from commercially available starting materials. Similarly, the thiazolyl compounds i.e. compound 17a may be prepared from the corresponding lithio or halo thiazole compound or synthons thereof. For example, the starting material 2-chloro-1,3-thiazole-5-carbonitrile may be prepared from 2-chloro-1,3-thiazole-5-carboxylic acid which may be purchased from Bionet Research Limited, Cornwall, PL329QZ, United Kingdom.

In another embodiment of the processes for making compounds of the invention, the amino side chain may be introduced as a pre-installed substituent on the A ring. For example, Scheme 7 shows the preparation of certain compounds of the invention wherein the amino side chain is introduced as part of the starting material constituting the A-ring.

Scheme 7

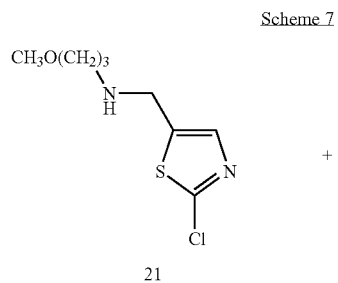

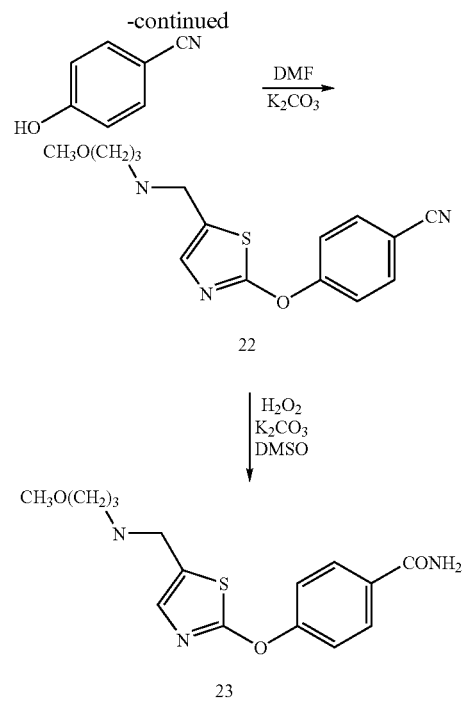

In Scheme 7, the starting material, 2-chloro-thiazol-5-yl-methyl)-(3-methoxy-propyl)-amine (21), may be purchased from Key Organics Limited/Bionet Research, Cornwall, UK. Analogs of the above starting material may be similarly purchased or prepared using known procedures. Reaction conditions and procedures for the coupling reaction and the subsequent hydrolysis of the nitrile to the amide have been disclosed in the experimental section and are also known to one of skill in the art.

Analogous to the procedure of Scheme 7, compounds wherein the $R^1$ and $R^2$ groups combine to form a nitrogen containing heterocycle may also be prepared using pre-installed cyclic amine groups on the A-ring as shown for example in Scheme 8.

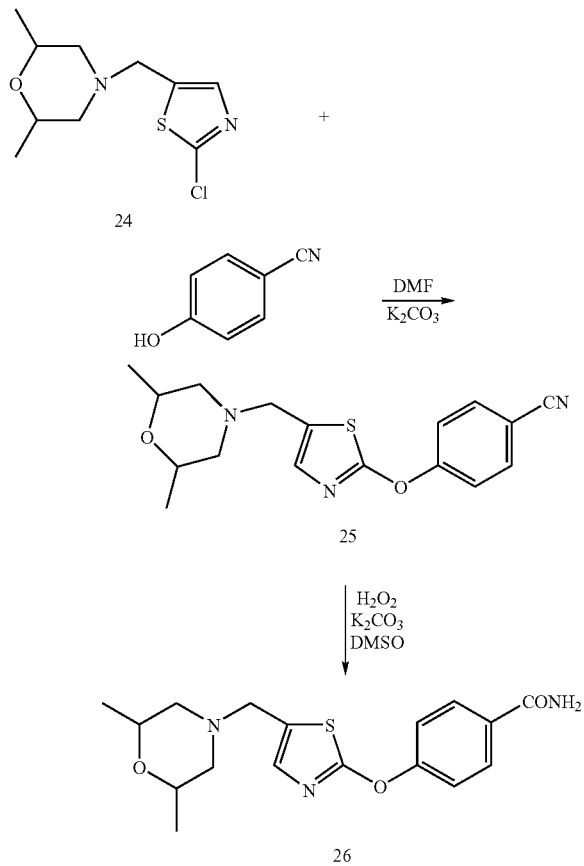

In an alternate procedure the thiazole starting material may be prepared as shown in Scheme 9 or knonwn variationn thereof.

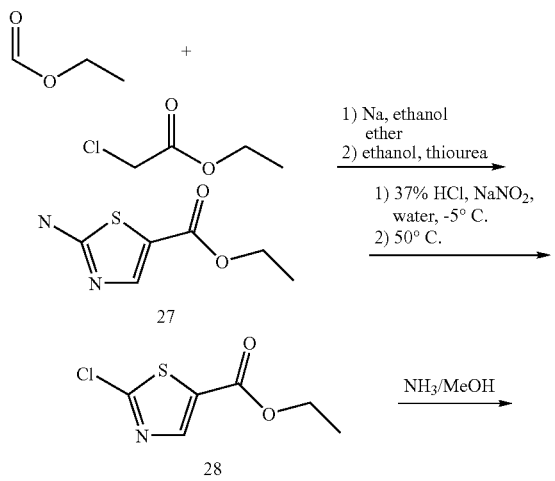

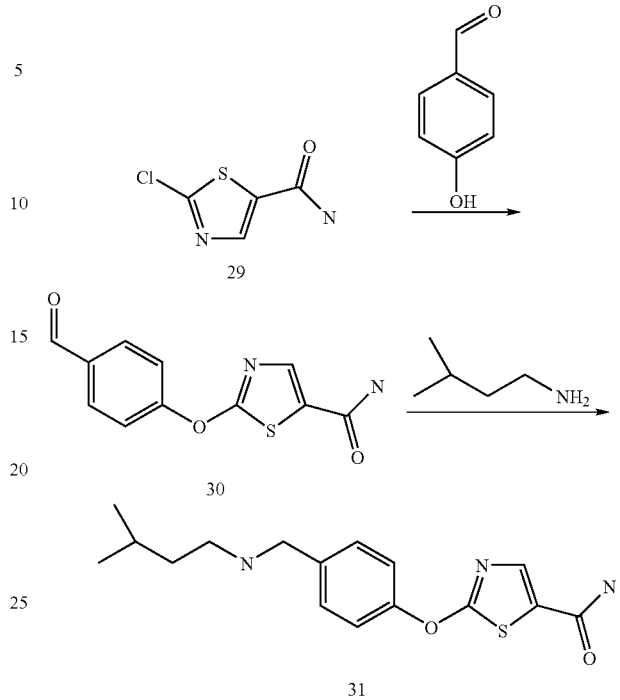

The preparation and use of the thiazole starting mateial according to scheme 9 begins with an aldol condensation of ethylfromate and ethylchloroacetate. The intermediate aldol condensation product is reacted with thiourea to afford the aminothiazole compound (27). The reaction is performed at temperatures ranging from about 70 to 90° C. The amino thaizole (27) is converted to the chlorothiazole compound diazoltization followed by chlorination as in the Sandmeyer reaction (see *Name Reactions and Reagents in Organic Synthesis* by Bradford P. Mundy and Michael Ellerd, John Wiley and Sons Publishers, New York, N.Y. 1988.) The resulting chlorothiazole ethyl ester (28) is aminated by bubbling excess ammonia into a cold methanolic solution of 28 to afford the carboxamide (29). The reaction is performed in a pressure vessael and may be heated to about 30 to 60° C. for 1 to 4 hours or as appropriate for complete reaction. The use of molecular sieves has also been found to facilitate the reactionat lower temperatures. The carboxamido chlorothiazole (29) is then reacted with, for example, 4-hydroxybenzaldehyde to afford the ether linkage. Depending on the ring desired, and appropriately substituted hydroxy carbaldehyde compound bearing the desired ring may be used to afford the ether linkage. The formation of the ether linkage has been discussed previously. The ether compound (30) may be reductively aminated at the carbonyl group with a desired amine compound e.g., isopentyl amine, to afford the desired compound (31).

The above procedures and minor modifications known to one of skill in the art are useful to prepapre other compounds of the invention.

Method of Using the Invention

As noted above, the compounds of the present invention are useful in blocking the effect of agonists at mu, kappa, and/or delta opioid receptors. As such, the present invention also provides a method for blocking a mu, kappa, delta receptor or receptor combination (heterodimer) thereof in mammals comprising administering to a mammal requiring blocking of a mu, kappa, delta or combinations of mu, kappa, and/or delta receptors, a receptor blocking dose of a compound of formula I.

The term "receptor blocking dose", as used herein, means an amount of a compound of formula I necessary to effectively block a mu, kappa, or delta receptor or receptor combination (heterodimer) thereof following administration to a mammal requiring blocking of a mu, kappa, or delta receptor or receptor combination (heterodimer) thereof.

The compounds of formula I or combinations thereof, are effective over a wide dosage range. For example, dosages per day will normally fall within the range of about 0.05 to about 50 mg/kg of body weight. In the treatment of adult humans, the range of about 0.5 to about 50 mg/kg, in single or divided doses, is preferred. However, it will be understood that the amount of the compound actually administered will be determined by a physician in light of the relevant circumstances, including the condition to be treated, the choice of compound to be administered, the age, weight, and response of the individual patient, the severity of the patient's symptoms, and the chosen route of administration, and therefore the above dosage ranges are not intended to limit the scope of the invention in any way. The compound(s) of the invention may be administered by a variety of routes such as the oral, transdermal, subcutaneous, sublingual, intranasal, intramuscular or intravenous routes.

A variety of physiologic functions have been shown to be subject to or influenced by mu, kappa, or delta receptors or receptor combination (heterodimers) in the brain. As such, the compounds of the present invention are believed to have the ability to treat a variety of disorders in mammals associated with these receptors or combinations thereof, such as eating disorders, opioid overdose, depression, smoking, alcoholism, sexual dysfunction, shock, stroke, spinal damage and bead trauma. As such, the present invention also provides methods of treating the above disorders by blocking the effect of agonists at a mu, kappa, delta receptor or receptor combination (heterodimer) thereof.

The compounds of the present invention have been found to display significant activity in an opioid receptor binding assay which measures the ability of the compounds to block the mu, kappa, delta or receptor combination (heterodimer) thereof.

GTP-γ-S Binding Assay

A scintillation proximity assay (SPA)-based GTP-γ-S$^{35}$ assay format was developed based on previous opioid (Emmerson et al., J. Pharm Exp Ther 278, 1121, 1996; Horng et al., Society for Neuroscience Abstracts, 434.6, 2000) and muscarinic (DeLapp et al., JPET 289, 946, 1999) assay formats. Membranes were resuspended in 20 mM HEPES, 100 mM NaCl, 5 mM MgCl2, 1 mM DTT, and 1 mM EDTA. Fifty mL of GTP-γ-[35S], compound, membrane suspension (20 microgram/well), and wheat germ agglutinin coated SPA beads (1 mg/well) were added to clear bottom 96 well assay plates. GDP (200 mM) was added to the membrane solution prior to addition to the assay plates. Plates were sealed and incubated for four hours at room temperature then placed in a refrigerator overnight to allow the beads to settle. Signal stability at 4° C. was determined to be >60 hours. Plates were warmed to room temperature and counted in a Wallac Microbeta scintillation counter. For antagonist assays, specific agonists were added at the following concentrations: (MOR) DAMGO 1 micromolar, (DOR) DPDPE 30 nM, (KOR) US69593 300 nM. Kb's were determined by Cheng-Prusoff equation (see Cheng and Prusoff, Biochem. Pharmacol. 22, 3099 1973).

TABLE 1

| | In Vitro Antagonism GTP-γ-S Kb (nM) | | |
|---|---|---|---|
| Example No. | Mu | Kappa | Delta |
| 1 | 0.6 | 4.6 | 3.3 |
| 2 | 3.7 | 2.2 | 19.4 |
| 3 | 0.6 | 3.9 | 1.6 |
| 4 | 0.6 | 1.0 | 2.7 |
| 5 | 0.6 | 1.4 | 2.4 |
| 6 | 5.7 | — | 13.7 |
| 7 | 0.3 | 4.0 | 1.3 |
| 8 | 4.7 | 3.2 | 40.5 |

Formulation

A compound of the invention is preferably presented in the form of a pharmaceutical formulation comprising a pharmaceutically acceptable carrier, diluent or excipient and a compound of the invention. Such compositions will contain from about 0.1 percent by weight to about 90.0 percent by weight of the compound of the invention (Active Ingredient). As such, the present invention also provides pharmaceutical formulations comprising a compound of the invention and a pharmaceutically acceptable carrier, diluent or excipient therefor.

In making the compositions of the present invention, the active ingredient will usually be mixed with a carrier, or diluted by a carrier, or enclosed within a carrier which may be in the form of a capsule, sachet, paper or other container. When the carrier serves as a diluent, it may be a solid, semi-solid or liquid material that acts as a vehicle, excipient or medium for the active ingredient. Thus, the composition can be in the form of tablets, pills, powders, lozenges, sachets, cachets, elixirs, emulsions, solutions, syrups, suspensions, aerosols (as a solid or in a liquid medium) and soft and hard gelatin capsules.

Examples of suitable carriers, excipients, and diluents include lactose, dextrose, sucrose, sorbitol, mannitol, starches, gum acacia, calcium phosphate, alginates, calcium silicate, microcrystalline cellulose, polyvinylpyrrolidone, cellulose, tragacanth, gelatin, syrup, methyl cellulose, methyl- and propylhydroxybenzoates, talc, magnesium stearate, water, and mineral oil. The formulations may also include wetting agents, emulsifying and suspending agents, preserving agents, sweetening agents or flavoring agents. The formulations of the invention may be formulated so as to provide quick, sustained, or delayed release of the active ingredient after administration to the patient by employing procedures well known in the aft.

For oral administration, the Active Ingredient, a compound of this invention ideally can be admixed with carriers and diluents and molded into tablets or enclosed in gelatin capsules.

The compositions are preferably formulated in a unit dosage form, each dosage containing from about 1 to about 500 mg, more usually about 5 to about 300 mg, of the Active Ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical carrier.

In order to more fully illustrate the operation of this invention, the following formulation examples are provided. The examples are illustrative only, and are not intended to limit the scope of the invention. The formulations may employ as Active Ingredient any of the compounds of the present invention.

FORMULATION 1
Hard gelatin capsules are prepared using the following ingredients:

| Compound | Amount per capsule (mg) | Concentration by weight (%) |
|---|---|---|
| Active Ingredient | 250 | 55 |
| Starch dried | 200 | 43 |
| Magnesium stearate | 10 | 2 |

The above ingredients are mixed and filled into hard gelatin capsules in 460 mg quantities.

FORMULATION 2
Capsules each containing 20 mg of medicament are made as follows:

| Compound | Amount per capsule (mg) | Concentration by weight (%) |
|---|---|---|
| Active Ingredient | 20 | 10 |
| Starch | 89 | 44.5 |
| Microcrystalline cellulose | 89 | 44.5 |
| Magnesium stearate | 2 | 1 |

The active ingredient, cellulose, starch and magnesium stearate are blended, passed through a No. 45 mesh U.S. sieve and filled into a hard gelatin capsule.

FORMULATION 3
Capsules each containing 100 mg of active ingredient are made as follows:

| Compound | Amount per capsule (mg) | Concentration by weight (%) |
|---|---|---|
| Active Ingredient | 100 | 30 |
| Polyoxyethylene Sorbitan monooleate | 50 mcg | 0.02 |
| Starch powder | 250 | 69.98 |

The above ingredients are thoroughly mixed and placed in an empty gelatin capsule.

FORMULATION 4
Tablets each containing 10 mg of active ingredient are prepared as follows:

| Compound | Amount per capsule (mg) | Concentration by weight (%) |
|---|---|---|
| Active Ingredient | 10 | 10 |
| Starch | 45 | 45 |
| Microcrystalline cellulose | 35 | 35 |
| Polyvinylpyrrolidone (as 10% solution in water) | 4 | 4 |
| Sodium carboxymethyl starch | 4.5 | 4.5 |
| Magnesium stearate | 0.5 | 0.5 |
| talc | 1 | 1 |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granule so produced is dried at 50-60° C. and passed through a No. 18 mesh U.S. sieve. The sodium carboxymethyl starch, magnesium stearate and talc, previously passed through a No. 60 mesh U.S. sieve, are then added to the granule which, after mixing, is compressed on a tablet machine to yield a tablet weighing 100 mg.

FORMULATION 5
A tablet formula may be prepared using the ingredients below:

| Compound | Amount per capsule (mg) | Percent by weight (%) |
|---|---|---|
| Active Ingredient | 250 | 38 |
| Cellulose microcrystalline | 400 | 60 |
| Silicon dioxide fumed | 10 | 1.5 |
| Stearic acid | 5 | 0.5 |

The components are blended and compressed to form tablets each weighing 665 mg.

FORMULATION 6
Suspensions each containing 5 mg of medicament per 5 ml dose are made as follows:

| Compound | Amount per 5 mL suspension (ml) |
|---|---|
| Active Ingredient | 5 |
| Sodium carboxymethyl cellulose | 50 |
| Syrup | 1.25 |
| Benzoic acid solution | 0.10 |
| Flavor | q.v. |
| Color | q.v. |
| Water | q.s. to 5 mL |

The medicament is passed through a No. 45 mesh U.S. sieve and mixed with the sodium carboxymethylcellulose and syrup to form a smooth paste. The benzoic acid solution, flavor and color is diluted with some of the water and added to the paste with stirring. Sufficient water is then added to produce the required volume.

FORMULATION 7
An aerosol solution is prepared containing the following components:

| Compound | Concentration by weight (percent) |
|---|---|
| Active Ingredient | 0.25 |
| Ethanol | 29.75 |
| Propellant 22 (chlorodifluoromethane) | 70.0 |

The active compound is mixed with ethanol and the mixture added to a portion of the Propellant 22, cooled to −30° C. and transferred to a filling device. The required amount is then fed to a stainless steel container and diluted further with the remaining amount of propellant. The valve units are then fitted to the container.

EXAMPLE 1

4-[5-(Phenethylamino-methyl)-thiophen-2-yloxy]-benzamide

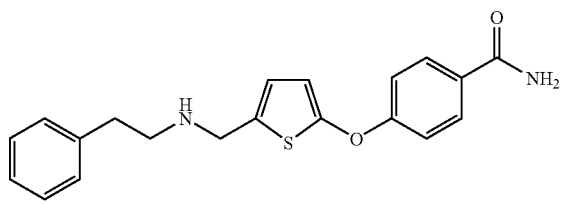

Part A, Method A:

Preparation of 4-(5-Formyl-thiophen-2-yloxy)-benzonitrile

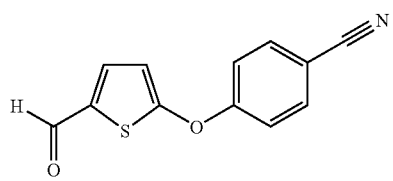

Combine 4-hydroxybenzonitrile (1.89 g, 15.07 mmol), sodium hydride (603 mg, 15.07 mmol) and DMSO (25 mL). Stir for 5-10 min at rt, then add 5-bromothiophene-2-carbaldehyde (1.5 mL, 12.56 mmol). Stir the reaction mixture at 100° C. overnight. Cool the reaction mixture to room temperature, then pour into water and extract thoroughly with diethyl ether (2×15 mL). Dry the organic layers over magnesium sulfate, filter and concentrate. Purify the crude product through flash chromatography using $CH_2Cl_2$/hexanes (2/1) as eluent to provide 500 mg (17%) of the title compound.

Part A, Method B:

Combine 4-hydroxybenzonitrile (1.37 g, 11.5 mmol), cesium carbonate (5.1 g, 15.69 mmol) and dimethylacetamide (DMA) (52 mL). Stir for 5 minutes at room temperature, and then add 5-bromothiophene-2-carbaldehyde (1.25 mL, 10.5 mmol). Stir the reaction mixture at 100° C. overnight. Cool the reaction mixture to room temperature, then pour into water and extract thorough with diethyl ether (2×30 mL). Dry the organic layers over magnesium sulfate, filter and concentrate. Purify the product through flash chromatography using $CH_2Cl_2$/hexanes (2/1) as eluent to provide 772 mg (32%) of the title compound.

Part B, Method A

Preparation of 4-[5-(Phenethylamino-methyl)-thiophen-2-yloxy]-benzonitrile

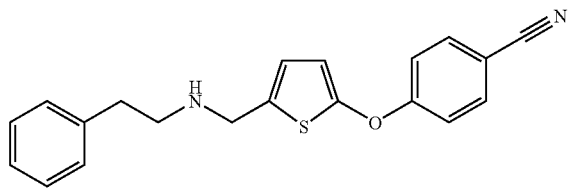

Combine 4-(5-formyl-thiophen-2-yloxy)-benzonitrile (200 mg, 0.87 mmol), $(MeO)_3CH$ (1.2 mL), phenethyl amine (0.142 mL, 130 mol %) and methanol (1.7 mL). Stir the resulting mixture for 3 hours, and then add sodium borohydride in portions. Stir for few hours. Then, concentrate to remove the methanol. Partition the resulting residue between $H_2O$ (5 mL) and $CH_2Cl_2$ (7 ml). Dry the organic layer over sodium sulfate, filter and concentrate. Purify the product through flash chromatography [$CH_2Cl_2$/Ammonia (2.0 M in methanol) 20/1] to provide the title compound (139 mg, 48%).

Part C, Method A

Combine 4-[5-(phenethylamino-methyl)-thiophen-2-yloxy]-benzonitrile ((139 mg, 0.415 mmol), $K_2CO_3$ (powder, 28 mg, 50 mol %) and DMSO (4 mL). Cool down to 0° C. Add hydrogen peroxide (0.124 mL) dropwise. Stir the resulting reaction mixture for 2.5 h. Partition the reaction mixture between $H_2O$ (5 mL) and $CH_2Cl_2$ (3×5 mL). Dry over sodium sulfate, filter and concentrate. Purify the residue through an SCX column with ammonia (2.0 M in methanol) to provide 105 mg (75%) of the title compound. Mass spectrum (ion spray): m/z=353.0 (M+1). $^1H$ NMR ($Cl_3CD$): 7.80 (d, J=8.7 Hz, 2H), 7.34-7.22 (m, 5H), 7.12 (d, J=8.7 Hz, 2H), 6.65 (d, J=3.37 Hz, 1H), 6.44 (d, J=3.7 Hz, 1H), 5.96 (bs, 2H), 3.93 (s, 2H), 2.97 (t, J=6.4 Hz, 2H), 2.85 (t, J=6.5 Hz, 2H).

Part B, Method B

Preparation of 4-(5-Formyl-thiophen-2-yloxy)-benzamide

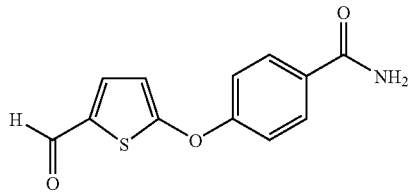

Combine 4-(5-formyl-thiophen-2-yloxy)-benzonitrile (772 mg, 3.36 mmol), $K_2CO_3$ (powder, 232 mg, 50 mol %) and DMSO (33 mL). Cool down to 0° C. Add hydrogen peroxide (1.01 mL) dropwise. Stir the resulting reaction mixture for 3 hours. Pour the reaction mixture onto $H_2O$ (5 mL). Stir for 5 min till a white precipitate appears, then filter and dry under vacuum to provide 633 mg (76%) of the title compound. Part C would be the reaction of this intermediate with an amine to make the final compound. Example 1 was prepared using Method A; Example 2 used Medthod B.

EXAMPLE 2

4-{5-[(3-Methyl-butylamino)-methyl]-thiophen-2-yloxy}-benzamide

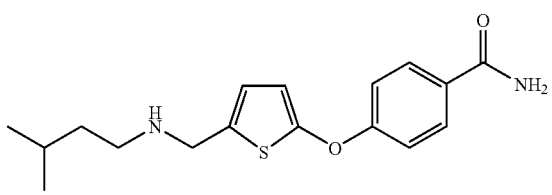

Combine 4-(5-formyl-thiophen-2-yloxy)-benzamide (99 mg, 0.40 mmol) from Example 1 part B, method B, with 3-methyl-butylamine (0.056 mL, 0.48 mmol), methyl orthoformate (0.53 mL) and methanol (0.8 mL). Stir the resulting mixture for 3 hours and then add sodium borohydride in portions. Let stir for few hours. Then, concentrate to remove the methanol. Partition the resulting residue between H$_2$O (4 mL) and CH$_2$Cl$_2$ (6 ml). Dry the organic layer over sodium sulfate, filter and concentrate. Purify through flash chromatography [CH$_2$Cl$_2$/Ammonia (2.0 M in methanol) 20/1] to provide the title compound.

EXAMPLE 3

4-(5-{[2-(3-Fluoro-phenyl)-ethylamino]-methyl}-thiophen-2-yloxy)-benzamide

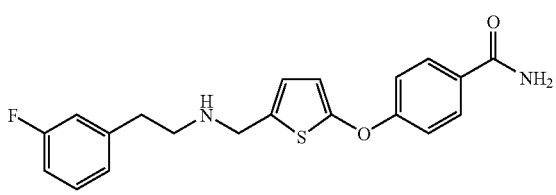

Combine 4-(5-formyl-thiophen-2-yloxy)-benzamide (90 mg, 0.36 mmol) from Example 1, part B, method B, with 2-(3-fluoro-phenyl)-ethylamine (61 mg, 0.44 mmol), methyl orthoformate (0.48 mL) and methanol (0.7 mL). Stir the resulting mixture for 3 hours and then add sodium borohydride in portions. Stir the reactiom misture until the reaction is complete by TLC or HPLC analyses. Then, concentrate to remove the methanol. Partition the resulting residue between H$_2$O (4 mL) and CH$_2$Cl$_2$ (6 ml). Dry the organic layer over sodium sulfate, filter and concentrate. Purify through flash chromatography [CH$_2$Cl$_2$/Ammonia (2.0 M in methanol) 20/1] to provide the title compound. $^1$H NMR (CDCl$_3$): 7.72 (d, J=8.7 Hz, 2H), 7.21-7.13 (m, 1H), 7.03 (d, J=8.7 Hz, 2H), 6.92-6.80 (m, 3H), 6.56 (d, J=3.6 Hz, 1H), 6.36 (d, J=3.7 Hz, 1H), 5.82 (bs, 2H), 3.83 (s, 2H), 2.87 (t, J=6.5 Hz, 2H), 2.75 (t, J=6.6 Hz, 2H).

EXAMPLE 4

4-{5-[(2-Cyclopentyl-ethylamino)-methyl]-thiophen-2-yloxy}-benzamide

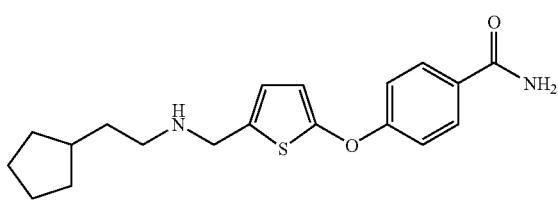

Using a method similar to Example 2, using 2-cyclopentyl-ethylamine (49 mg, 0.437 mmol) gives the title compound. $^1$H NMR (CDCl$_3$): 7.82 (d, J=8.7 Hz, 2H), 7.14 (d, J=8.7 Hz, 2H), 6.79 (d, J=3.3 Hz, 1H), 6.49 (d, J=3.7 Hz, 1H), 6.47 (bs, 2H), 3.92 (s, 2H), 2.80-2.67 (m, 2H), 1.79-1.54 (m, 9H).

EXAMPLE 5

4-{5-[(2-Thiophen-2-yl-ethylamino)-methyl]-thiophen-2-yloxy}-benzamide

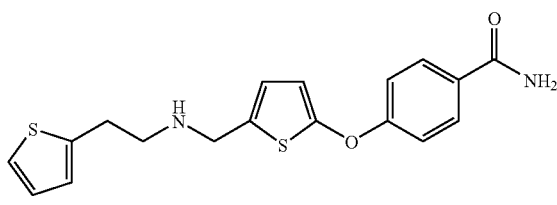

Using a method similar to Example 2, using 2-thiophen-2-yl-ethylamine (55 mg, 0.436 mmol) gives the title compound. $^1$H NMR (CDCl$_3$): 7.71 (d, J=8.7 Hz, 2H), 7.08-7.02 (m, 3H), 6.87-6.85 (m, 1H), 6.77 (d, J=2.8 Hz, 1H), 6.58 (d, J=3.5 Hz, 1H), 6.36 (d, J=3.6 Hz, 1H), 5.80 (bs, 2H), 3.85 (s, 2H), 2.97-2.90 (m, 4H).

EXAMPLE 6

4-{5-[(3,3-Dimethyl-butylamino)-methyl]-thiophen-2-yloxy}-benzamide

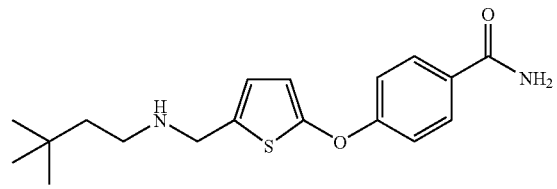

Using a method similar to Example 2, using 3,3-dimethyl-butylamine (0.049 mL, 0.361 mmol) gives the title compound (87 mg, 76%). m/z=232.0 (M+1). $^1$H NMR (DMSO-d$_6$): 7.90 (bs, 3H), 7.30 (s, 1H), 7.1 (bs, 2H), 6.72 (s, 1H), 6.55 (s, 1H), 3.78 (s, 2H), 3.32 (s, 2H), 1.32 (s, 2H), 0.85 (s, 9H).

EXAMPLE 7

3-Methoxy-4-[5-(phenethylamino-methyl)-thiophen-2-yloxy]-benzamide hydrochloride

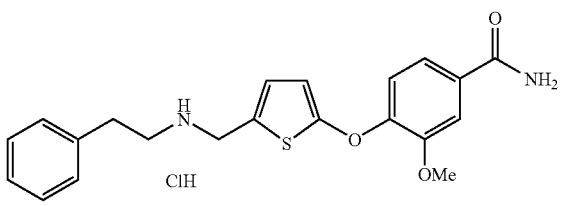

Step 1

Preparation of 4-(5-Formyl-thiophen-2-yloxy)-3-methoxy-benzonitrile

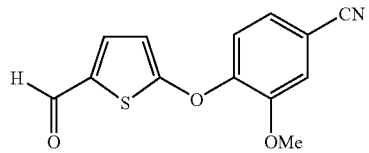

Using a method similar to preparation of the compound of Example 1 part A, method A, and using 4-hydroxy-3-methoxy-benzonitrile (859 mg, 5.76 mmol) gives the title compound (225 mg, 17%). ¹H NMR (Cl₃CD): 9.71 (s, 1H), 7.54 (d, J=4.1 Hz, 1H), 7.30 (d, J=8.1 Hz, 1H), 7.28 (s, 1H), 7.23 (d, J=8.1 Hz, 1H), 6.53 (d, J=4.2 Hz, 1H), 3.89 (s, 3H).

Step 2

Preparation of 4-(5-Formyl-thiophen-2-yloxy)-3-methoxy-benzamide

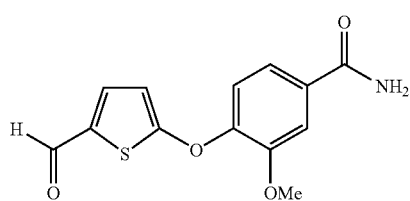

Using a method similar to example 1, part B, method B, and using 4-(5-formyl-thiophen-2-yloxy)-3-methoxy-benzonitrile (225 mg, 0.867 mmol) gives the title compound.

Step 3

Using a method similar to Example 2, using phenethylamine (0.082 mL, 0.649 mmol) and 4-(5-formyl-thiophen-2-yloxy)-3-methoxy-benzamide (150 mg, 0.54 mmol) gives the title compound. ¹H NMR (MeOH-d₄): 7.62 (d, J=1.9 Hz, 1H), 7.47 (dd, J=1.9 and 8.4 Hz, 1H), 7.32-7.19 (m, 5H), 7.10 (d, J=8.3 Hz, 1H), 6.78 (d, J=3.7 Hz, 1H), 6.39 (d, J=3.8 Hz, 1H), 3.99 (s, 2H), 3.91 (s, 3H), 2.99-2.84 (m, 4H).

EXAMPLE 8

3-Methoxy-4-{5-[(3-methyl-butylamino)-methyl]-thiophen-2-yloxy}-benzamide hydrochloride

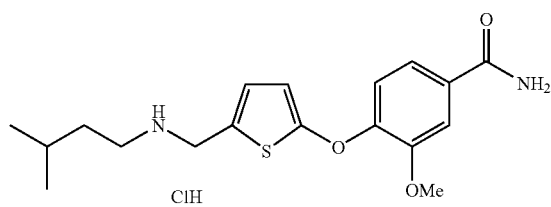

Using a method similar to Example 2, using 3-methyl-butylamine (0.050 mL, 0.432 mmol) and 4-(5-formyl-thiophen-2-yloxy)-3-methoxy-benzamide (100 mg, 0.36 mmol) gives the title compound. ¹H NMR (DMSO-d₆): 7.65 (d, J=1.9 Hz, 1H), 7.49 (dd, J=1.9 and 8.3 Hz, 1H), 7.22 (bd, 1H), 7.17 (d, J=8.3 Hz, 1H), 7.01 (d, J=3.9 Hz, 1H), 6.99 (bd, 1H), 6.45 (d, J=3.9 Hz, 1H), 4.31 (bs, 2H), 3.91 (s, 3H), 3.31 (m, 2H), 1.62-1.57 (m, 3H), 0.97 (d, J=6.4 Hz, 6H).

EXAMPLE 9

4-[5-(2-Phenethylamino-ethyl)-thiophen-2-yloxy]-benzamide hydrochloride

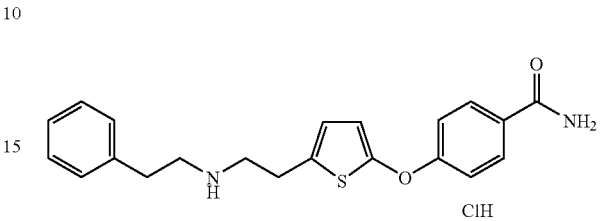

Step 1

Preparation of 4-[5-(2-Oxo-ethyl)-thiophen-2-yloxy]-benzonitrile

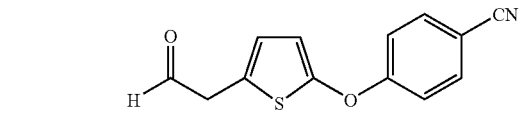

Combine a solution of methoxy methyl triphenyl phosphonium chloride (358 mg, 1.047 mmol) in THF (3.6 mL) with a solution of KHMDS (0.5M in toluene, 2 mL, 1.047 mmol) at 0° C. for 20-40 min. Cool the resulting orange solution to about −78° C., then add a solution of 4-(5-formyl-thiophen-2-yloxy)-benzonitrile in THF (1 mL) dropwise over about 10 min. Stir at about −78° C. for 45 min, then allow the reaction mixture to warm to room temprature and quench with H₂O (5 mL). Extract the reaction mixture with ether (5 mL), wash with H₂O, dry over magnesium sulfate, filter and concentrate. Purify the crude product by flash chromatography (CH₂Cl₂) to provide 155 mg of 4-[5-(2-methoxy-vinyl)-thiophen-2-yloxy]-benzonitrile. Redissolve the product in i-PrOH (about 0.8 mL)—H₂O (about 0.8 mL) and add pTsOH.H₂O (4 mg, 0.018 mmol). Stir the reaction mixture at reflux for 2-3 hours. Cool the reaction mixture to room temprature, dilute with H₂O (5 mL) and extract with diethyl ether (6 mL). Wash the organic layer with sodium bicarbonate, brine, dry over magnesium sulfate, filter and concentrate under reduced pressure to give the title compound.

Step 2

4-[5-(2-Phenethylamino-ethyl)-thiophen-2-yloxy]-benzonitrile

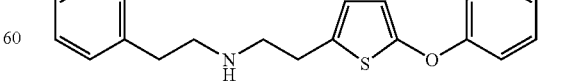

Using a method similar to preparation of the compound of Example 1 part B, method A, and using phenethyl amine (0.022 mL, 0.17 mmol) gives the title compound (25 mg, 55%).

Step 3

4-[5-(2-Phenethylamino-ethyl)-thiophen-2-yloxy]-benzamide hydrochloride

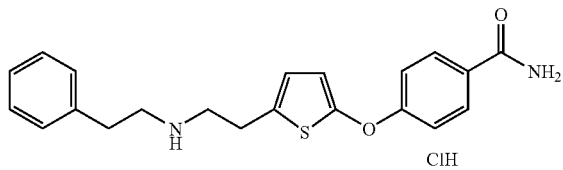

Using a method similar to Example 1, and using 4-[5-(2-phenethylamino-ethyl)-thiophen-2-yloxy]-benzonitrile (25 mg, 0.072 mmol) gives the title compound as the free base. Treatment with HCl (1M in ether) provides the hydrochloride salt.

EXAMPLE 10

5-{4-[(3-Methylbutylamino)methyl]phenoxy}thiophene-2-carboxamide

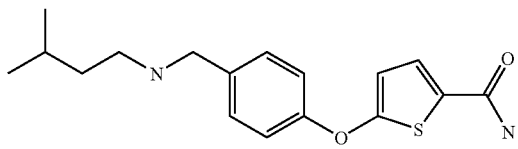

Part A: 5-Fluorothiophene-2-carbonitrile

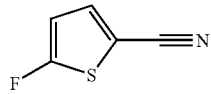

Reference: Chambers, R. J.; Marfat, A. *Synth. Commun.*, 2000, 30 (19), 3629-3632.

Mix 2-cyano-5-nitrothiophene (1.000 g, 6.49 mmol), spray dried KF (1.885 g, 32.43 mmol), tetraphenylphosphonium bromide (0.250 g, 0.597 mmol) and phthaloyl dichloride (0.935 mL-6.49 mmol) in sulfolane (20 mL) and heat at 180° C. After two hours, cool to room temperature, then dilute with water (100 mL) and extract with ether (3×100 mL). Wash the extract with 1.0 N NaOH (1×50 mL) and brine (1×50 mL). Dry the organic layer over MgSO$_4$, filter and concentrate. Purify by chromatography eluting with 10% EtOAc in hexanes to give the title compound: $^1$H NMR (CDCl$_3$): 7.33 (t, J=4.0 Hz, 1H), 6.56 (dd, J=4.4, 1.8 Hz, 1H); HPLC [YMC-Pro pack C-18 (150×4.6 mm, S-5 microm), 0.05% TFA/acetonitrile in 0.05% TFA/water at 1.0 mL/min, 30-99% over 18 min], $t_R$=7.3 min, 94.1% purity.

Part B: 5-(4-Formylphenoxy)thiophene-2-carbonitrile

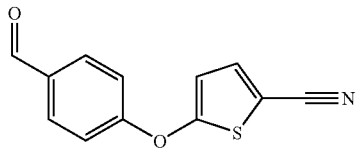

Dissolve 5-fluorothiophene-2-carbonitrile (0.541 g, 4.25 mmol) and 4-hydroxybenzaldehyde (0.519 g, 4.25 mmol) in DMF (11 mL). Add K$_2$CO$_3$ (1.469 g, 10.6 mmol) and heat at 100° C. for 1.5 hours. Concentrate the reaction mixture. Take the solid up in ethyl acetate (100 mL) and wash with water (2×25 mL). Dry the organic layer over MgSO$_4$, filter and concentrate. Purify by chromatography eluting with 30% ethyl acetate in hexanes to give the title compound: $^1$H NMR (CDCl$_3$): 9.96 (s, 1H), 7.98 (dd, J=6.6, 2.2 Hz, 2H), 7.86 (d, J=4.0 Hz, 1H), 7.40 (d, J=2.2 Hz, 2H), 6.96 (d, J=4.0 Hz, 1H); HPLC [YMC-Pro pack C-18 (150×4.6 mm, S-5 microm), 0.05% TFA/acetonitrile in 0.05% TFA/water at 1.0 mL/min, 10-20% over 5 min, 20-95% over 18], $t_R$=17.4 min, 98.1% purity.

Part C: 5-(4-Formylphenoxy)thiophene-2-carboxamide

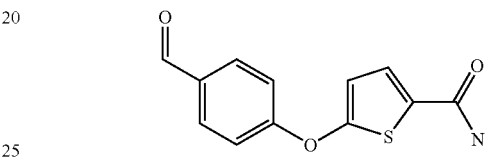

Dissolve 5-(4-formylphenoxy)thiophene-2-carbonitrile (0.818 g, 3.57 mmol) in DMSO (18 mL) in a round bottom flask, then add K$_2$CO$_3$ (0.247 g, 1.78 mmol). Cool the reaction flask in a water bath and add 30% H$_2$O, (0.81 mL, 7.14 mmol) solution. After one hour, add water (25 mL). Filter the resulting precipitate and wash the filter cake with water (25 mL). Collect the filter cake as the title compound: HRMS calcd for C$_{12}$H$_{10}$NO$_3$S 248.0381 (M+H)$^+$, found 248.0396, time 0.36 min; HPLC [YMC-Pro pack C-18 (150×4.6 mm, S-5 microm), 0.05% TFA/acetonitrile in 0.05% TFA/water at 1.0 mL/min, 10-20% over 5 min, 20-95% over 18], $t_R$=13.0 min, 100% purity.

Part D: 5-{4-[(3-Methylbutylamino)methyl]phenoxy}thiophene-2-carboxamide

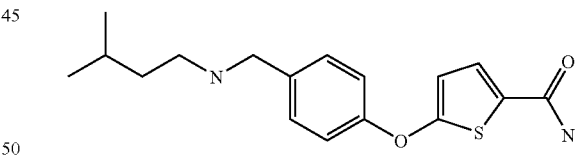

Place 5-(4-formylphenoxy)thiophene-2-carboxamide (0.235 g, 0.948 mmol), isoamylamine (0.087 g, 0.996 mmol) and 3 Å molecular sieves in a vial. Add methanol (4.7 mL), cap and stir overnight. Add NaBH$_4$ (0.0359 g, 0.948 mmol) and stir until the gasses stop evolving. Load the reaction mixture directly onto a 25 g ISCO® pre-load column. Dry the column in a vacuum oven at room temperature. Purify by eluting through a 40 g ISCO® column with 5% to 20% (2.0 M NH$_3$ in methanol) in ethyl acetate over 45 minutes to give the title compound: TOF MS ES$^+$ 319.1 (M+H)$^+$, HRMS calcd for C$_{17}$H$_{23}$N$_2$O$_2$S 319.1480 (M+H)$^+$, found 319.1488, time 0.38 min; HPLC [YMC-Pro pack C-18 (150×4.6 mm, S-5 microm), 0.05% TFA/acetonitrile in 0.05% TFA/water at 1.0 mL/min, 10-20% over 5 min, 20-95% over 18], $t_R$=10.8 min, 100% purity.

EXAMPLE 11

5-{4-[(3-Ethylpentylamino)methyl]phenoxy}thiophene-2-carboxamide

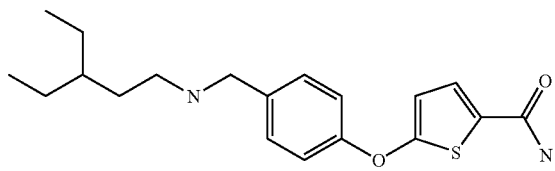

Part A: 3-Ethylpentanenitrile

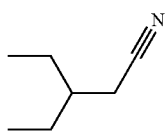

To a suspension of sodium cyanide (3.33 g, 67.8 mmol) in DMSO (24 mL) at 60° C., slowly add 1-bromo-2-ethylbutane (10 g, 60.6 mmol). Keep the internal temperature between 55-60° C. by intermittently cooling with an ice bath. Add additional DMSO (10 mL) to keep the slurry stirring. Heat at 70° C. for two hours, then cool to room temperature. Dilute the reaction mixture with water (100 mL) and extract with ether (3×50 mL). Wash the organic extracts with 5.0 N HCl (1×25 mL) and water (1×25 mL). Dry the organic layer over MgSO$_4$, filter and concentrate to give the title compound: $^1$H NMR (CDCl$_3$): 2.34 (d, J=6.2 Hz, 2H), 1.56 (m, 1H), 1.46 (m, 4H), 0.93 (t, J=7.3 Hz, 6H).

Part B: 3-Ethylpentylamine

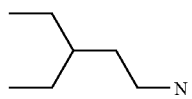

Cool a slurry of LiAlH$_4$ (4.35 g, 115 mmol) in ether (57 mL) to 0° C. Allow reaction mixture to gently reflux upon the addition of 3-ethylpentanenitrile (6.38 g, 57.3 mmol). Stir for two hours before quenching with 1.0 N NaOH. Filter the suspension through a Celite® pad. Separate the two layers and wash the organic layer with additional 1.0 N NaOH (2×25 mL), dry it over Na$_2$SO$_4$, filter and carefully concentrate to give the title compound: $^1$H NMR (DMSO-d$_6$): 2.50 (t, J=7.3 Hz, 2H), 1.24 (m, 7H), 0.080 (t, J=7.0 Hz, 6H).

Part C. 5-{4-[(3-Ethylpentylamino)methyl]phenoxy}thiophene-2-carboxamide

Place 5-(4-formylphenoxy)thiophene-2-carboxamide (Example 10, Part C) (0.235 g, 0.948 mmol), 3-ethylpentylamine (Part B) (0.115 g, 0.996 mmol) and 3 Å molecular sieves in a vial. Add methanol (4.7 mL), cap and stir overnight. Add NaBH$_4$ (0.0359 g, 0.948 mmol) and stir until the gasses stop evolving. Load the reaction mixture directly onto a 25 g ISCO® pre-load column. Dry the column in a vacuum oven at room temperature. Purify by eluting through a 40 g ISCO® column with 5% to 20% (2.0 M NH$_3$ in methanol) in ethyl acetate over 45 minutes to give the title compound: TOF MS ES$^+$ 347.2 (M+H)$^+$, HRMS calcd for C$_{19}$H$_{27}$N$_2$O$_2$S 347.1793 (M+H)$^+$, found 347.1799, time 0.38 min; HPLC [YMC-Pro pack C-18 (150×4.6 mm, S-5 microm), 0.05% TFA/acetonitrile in 0.05% TFA/water at 1.0 mL/min, 10-20% over 5 min, 20-95% over 18], t$_R$=12.4 min, 100% purity.

EXAMPLE 12

5-(4-{[2-(Tetrahydropyran-4-yl)ethylamino]methyl}phenoxy)thiophene-2-carboxamide

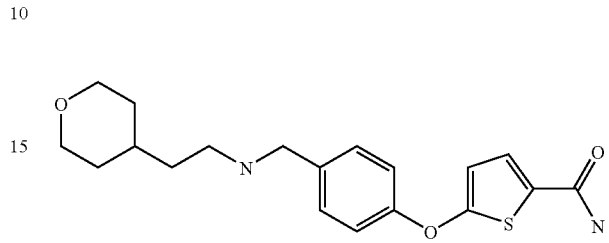

Place 5-(4-formylphenoxy)thiophene-2-carboxamide (Example 10, Part C) (0.235 g, 0.948 mmol), 2-(tetrahydropyran-4-yl)ethylamine (0.122 g, 0.996 mmol) and 3 Å molecular sieves in a vial. Add methanol (4.7 mL), cap and stir overnight. Add NaBH$_4$ (0.0359 g, 0.948 mmol) and stir until the gasses stop evolving. Load the reaction mixture directly onto a 25 g ISCO® pre-load column. Dry the column in a vacuum oven at room temperature. Purify by eluting through a 40 g ISCO® column with 5% to 30% (2.0 M NH$_3$ in methanol) in ethyl acetate over 45 minutes to give the title compound: TOF MS ES$^+$ 361.2 (M+H)$^+$, HRMS calcd for C$_{19}$H$_{25}$N$_2$O$_3$S 361.1586 (M+H)$^+$, found 361.1604, time 0.36 min; HPLC [YMC-Pro pack C-18 (150×4.6 mm, S-5 microm), 0.05% TFA/acetonitrile in 0.05% TFA/water at 1.0 mL/min, 10-20% over 5 min, 20-95% over 18], t$_R$=9.4 min, 100% purity.

EXAMPLE 13

2-{4-[(3-Methylbutylamino)methyl]phenoxy}thiazole-5-carboxamide

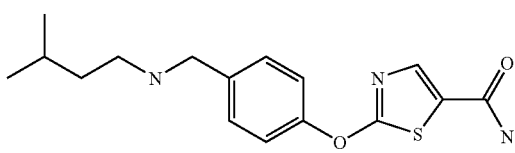

Part A: Ethyl 2-aminothiazole-5-carboxylate

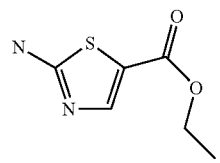

Reference: Plouvier, B.; Bailly, C.; Houssin, F.; Henichart, J. P. *Heterocycles,* 1991, 32 (4) 693-701.

Dissolve sodium (4.60 g, 200 mmol) in ethanol (100 mL). Cool the solution to −5° C. to −10° C. and add a mixture of ethyl formate (16.8 mL, 220 mmol) and ethyl chloroacetate (27.0 mL, 220 mmol). A white precipitate forms. Add ether (200 mL) to facilitate the precipitation. Warm the reaction mixture to room temperature and stir over night. Filter the precipitate and wash it with ether. Concentrate the filtrate to about ¼ of the volume, add ether (100 mL) and refilter. Dissolve the combined filter cakes with 10% HCl (100 mL). Extract the acidic aqueous phase with ether (3×100 mL). Dry the organic layer over $Na_2SO_4$, filter and concentrate. Dilute the liquid with ethanol (106 mL) and add thiourea (8.07 g 106 mmol). Heat the reaction mixture to 80° C. After 1.25 hours, concentrate the reaction mixture. Then take the dark oil up in 1.0 N NaOH (100 mL) and extract with dichloromethane (3×100 mL). Dry the organic extracts over $Na_2SO_4$, filter and concentrate. Suspend the solid with methanol, then add chloroform. Filter the resulting precipitate as the title compound: TOF MS ES$^+$ 173.0 (M+H)$^+$, HRMS calcd for $C_6H_9N_2O_2S$ 173.0385 (M+H)$^+$, found 173.0381, time 0.36 min; HPLC [YMC-Pro pack C-18 (150×4.6 mm, S-5 microm), 0.05% TFA/acetonitrile in 0.05% TFA/water at 1.0 mL/min, 10-20% over 5 min, 20-95% over 18], $t_R$=6.2 min, 100% purity.

Part B: Ethyl 2-chlorothiazole-5-carboxylate

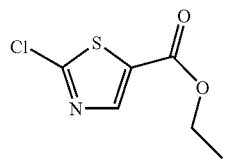

Reference: Potts, K. T.; Huseby, R. M. *J. Org. Chem.*, 1966, 31, 3528-3531.

Dissolve ethyl 2-aminothiazole-5-carboxylate (2.000 g, 11.6 mmol) in 37% HCl (58 mL) at −5° C. Slowly add a solution of sodium nitrite (0.962 g, 13.9 mmol) in water (11.6 mL). Maintain a temperature of −5° C. to −10° C. After 2.5 hours, heat the reaction mixture at 50° C. for additional 2 hours. Cool the reaction mixture to room temperature, then extract with ether (3×100 mL). Wash the organic extract with brine (1×70 mL), dry it over $MgSO_4$, filter and concentrate. Purify by chromatography eluting with 10% ether in hexanes to give the title compound: $^1$H NMR (CDCl$_3$): 8.14 (s, 1H), 4.36 (q, J=7.0 Hz, 2H), 1.38 (t, J=7.0 Hz, 3H); HPLC [YMC-Pro pack C-18 (150×4.6 mm, S-5 microm), 0.05% TFA/acetonitrile in 0.05% TFA/water at 1.0 mL/min, 10-20% over 5 min, 20-95% over 18], $t_R$=16.5 min, 100% purity.

Part C: 2-Chlorothiazole-5-carboxamide

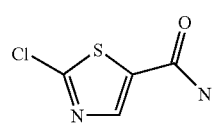

Dissolve ethyl 2-chlorothiazole-5-carboxylate (0.927 g, 4.84 mmol) in methanol. Cool the solution to 0° C., then bubble NH$_3$ into the reaction mixture for 10 minutes. Then seal the reaction vessel and stir for 3 hours. Concentrate the reaction mixture to give the title product: $^1$H NMR (CDCl$_3$): 8.21 (s, 1H), 8.19 (s, 1H), 7.77 (s, 1H); HPLC [YMC-Pro pack C-18 (150×4.6 mm, S-5 microm), 0.05% TFA/acetonitrile in 0.05% TFA/water at 1.0 mL/min, 10-20% over 5 min, 20-95% over 18], $t_R$=6.9 min, 100% purity.

Part D: 2-(4-Formylphenoxy)thiazole-5-carboxamide

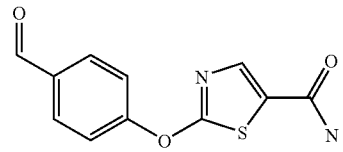

Dissolve 2-chlorothiazole-5-carboxamide (0.771 g, 4.78 mmol) and 4-hydroxybenzaldehyde (0.584 g, 4.78 mmol) in DMF (15.9 mL). Add $K_2CO_3$ (1.651 g, 11.95 mmol) and heat at 100° C. for 2 hours. Concentrate the reaction mixture. Take the solid up in dichloromethane:methanol (5:1). Add ethyl acetate to precipitate out a white solid. Filter and collect the solid as the title compound: $^1$H NMR (DMSO): 10.00 (s, 1H), 8.11 (s, 1H), 8.02 (d, J=8.4 Hz, 2H), 7.94 (s, 1H), 7.59 (d, J=8.8 Hz, 2H), 7.41 (s, 1H); HPLC [YMC-Pro pack C-18 (150×4.6 mm, S-5 microm), 0.05% TFA/acetonitrile in 0.05% TFA/water at 1.0 mL/min, 10-20% over 5 min, 20-95% over 18], $t_R$=11.4 min, 98.2% purity.

Part E: 2-{4-[(3-Methylbutylamino)methyl]phenoxy}thiazole-5-carboxamide

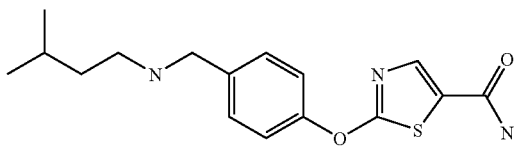

Place 2-(4-formylphenoxy)thiazole-5-carboxamide (0.187 g, 0.755 mmol), isoamylamine (0.072 g, 0.831 mmol) and 3 Å molecular sieves in a vial. Add methanol (3.8 mL), cap and stir overnight. Add NaBH$_4$ (0.029 g, 0.755 mmol) and stir until the gasses stop evolving. Load the reaction mixture directly onto a 25 g ISCO® pre-load column. Dry the column in a vacuum oven at room temperature. Purify by eluting through a 40 g ISCO® column with 5% (2.0 M NH$_3$ in methanol) in ethyl acetate over 45 minutes to give the title compound: TOF MS ES$^+$ 320.1 (M+H)$^+$, HRMS calcd for $C_{16}H_{22}N_3O_2S$ 320.1432 (M+H)$^+$, found 320.1428, time 0.32 min; HPLC [YMC-Pro pack C-18 (150×4.6 mm, S-5 microm), 0.05% TFA/acetonitrile in 0.05% TFA/water at 1.0 mL/min, 10-20% over 5 min. 20-95% over 18], $t_R$=9.7 min, 96.9% purity.

EXAMPLE 14

2-(4-{[2-(Tetrahydropyran-4-yl)ethylamino]
methyl}phenoxy)thiazole-5-carboxamide methane-
sulfonate

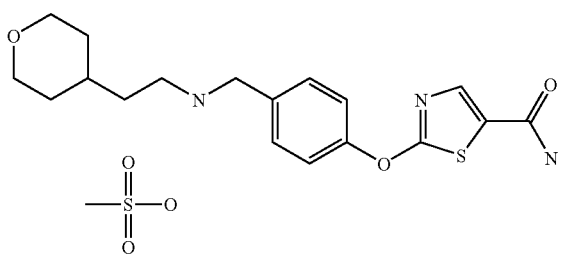

Place 2-(4-formylphenoxy)thiazole-5-carboxamide (Example 12, Part D) (0.187 g, 0.755 mmol), 2-(tetrahydropyran-4-yl)ethylamine (0.101 g, 0.831 mmol) and 3 Å molecular sieves in a vial. Add methanol (3.8 mL), cap and stir overnight. Add NaBH$_4$ (0.029 g, 0.755 mmol) and stir until the gasses stop evolving. Load the reaction mixture directly onto a 25 g ISCO® pre-load column. Dry the column in a vacuum oven at room temperature. Purify by eluting through a 40 g ISCO® column with 10% (2.0 M NH$_3$ in methanol) in ethyl acetate over 45 minutes to give the title compound as a free base. Dissolve the compound in dichloromethane:methanol (2:1) (3 mL) and add 1 equivalent of 0.50 M methanesulfonic acid in dichloromethane. Stir the solution for a short time before concentrating to give the title compound: TOF MS ES$^+$ 362.1 (M+H)$^+$, HRMS calcd for C$_{18}$H$_{24}$N$_3$O$_3$S 362.1538 (M+H)$^+$, found 362.1536, time 0.32 min; HPLC [YMC-Pro pack C-18 (150×4.6 mm, S-5 microm), 0.05% TFA/acetonitrile in 0.05% TFA/water at 1.0 mL/min, 10-20% over 5 min, 20-95% over 18], t$_R$=8.0 min, 95.0% purity.

EXAMPLE 15

4-{5-[(3-Methyl-butylamino)-methyl]-furan-2-yloxy}-benzamide

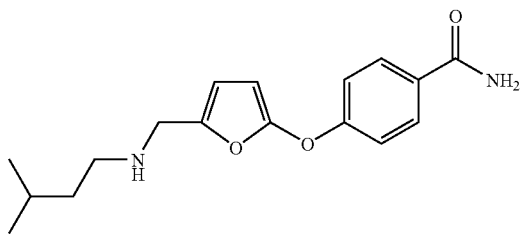

Part A: 4-(5-Formyl-tetrahydro-furan-2-yloxy)-benzonitrile

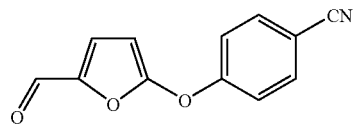

Combine 5-bromo-2-furaldehyde (3.96 g, 32.7 mmol), 4-hydroxybenzaldehyde (1.75 g, 10 mmol), DMF (100 mL), and potassium carbonate (2.07 g, 15 mmol), stir, and heat to 120° C. under nitrogen. After 18 hours, cool to ambient temperature, partially remove the solvent in vacuo, and dilute with 300 mL of water. Extract the aqueous solution with ethyl acetate (2×200 mL), wash the organic phase with brine (100 mL). Dry the organic phase over magnesium sulfate, filter, and concentrate under vacuum. Purify via ISCO 100 c system (120 g silica column), using a gradient: 80:20 hexane/ethyl acetate to 60:40 hexane/ethyl acetate to give the title compound (1.0 g, 46%) as a white solid: $^1$H NMR (chloroform-d): 9.5 (s, 1H), 7.71 (d, J=9 Hz, 2H), 7.18-7.27 (m, 3H), 5.84 (d, J=4 Hz, 1H).

Part B: 4-(5-Formyl-furan-2-yloxy)-benzamide

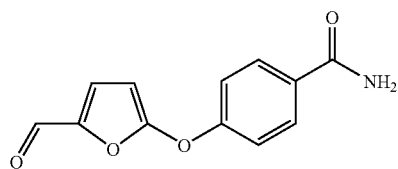

Combine 4-(5-Formyl-tetrahydro-furan-2-yloxy)-benzonitrile (1.0 g, 4.69 mmol), dimethylsufoxide (100 mL), potassium carbonate (0.32 g, 2.35 mmol), and 1 mL of 30% hydrogen peroxide solution. Stir 18 hours at ambient temperature. Dilute with 300 mL of ice/water, extract with ethyl acetate (3×150 mL). Wash the organic phase with 100 mL of water, and 100 mL of brine. Dry the organic phase over sodium sulfate, filter, and concentrate under vacuum. Purify via ISCO™ 100 c system using a gradient of 75:25 hexane/ethyl acetate to 25:75 hexane/ethyl acetate as eluting solvent to give 0.18 g (18%) of the title compound: $^1$H NMR (DMSO-d$_6$): 9.38 (s, 1H), 7.6 (d, 1H, J=3.8 Hz), 7.30-7.40 (m, 3H), 6.0 (d, 2H, J=3.7 Hz).

Part C:

4-{5-[(3-Methyl-butylamino)-methyl]-furan-2-yloxy}-benzamide

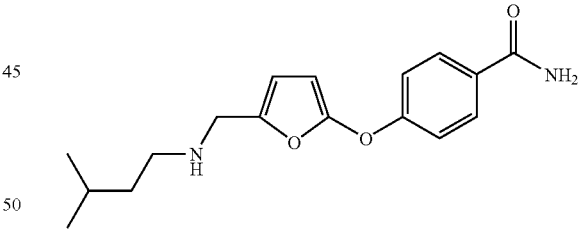

Combine 4-(5-Formyl-furan-2-yloxy)-benzamide (0.18 g, 0.78 mmol), isoamylamine (0.10 g, 0.1.17 mmol), 3 Å molecular sieves (2 g) in methanol (30 mL), agitate 18 hours at ambient temperature. Add sodium borohydride (0.058 g, 1.52 mmol), agitate 20 hours at ambient temperature. Filter through Celite, then concentrate in vacuo. Partition the residue between water (50 mL), and ethyl acetate (150 mL). Drain the organic layer, and dry over sodium sulfate. Purify via ISCO™ 100 c (40 g silica) using a gradient of 95:5:0.5 to 90:10:1 chloroform/ethanol/ammonium hydroxide to afford the title compound (0.160 g, 68%): mass spectrum (ion spray): m/z=303.18 (M+1); HPLC retention time: 5.79 min (HPLC method in this experiment: 5:95-95:5 ACN/0.1% TFA in water over 10 minutes using a 15 cm Zorbax column, running at 1 mL/minute, ultraviolet detector set at 254 nM).

We claim:
1. A compound selected from the group consisting of:
4-[5-(Phenethylamino-methyl)-thiophen-2-yloxy]-benzamide

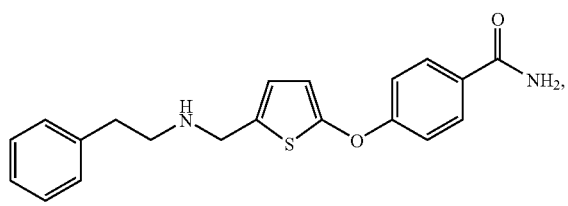

4-{5-[(3-Methyl-butylamino)-methyl]-thiophen-2-yloxy}-benzamide

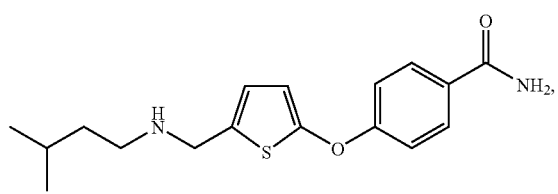

4-(5-{[2-(3-Fluoro-phenyl)-ethylamino]-methyl}-thiophen-2-yloxy)-benzamide

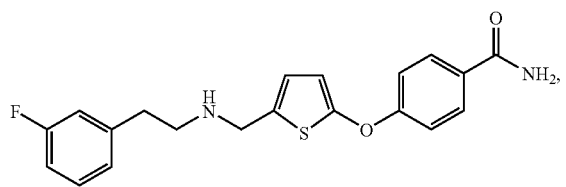

4-{5-[(2-Cyclopentyl-ethylamino)-methyl]-thiophen-2-yloxy}-benzamide

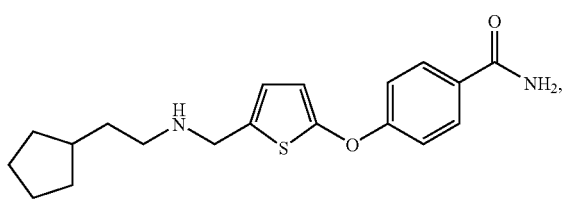

4-{5-[(2-Thiophen-2-yl-ethylamino)-methyl]-thiophen-2-yloxy}-benzamide

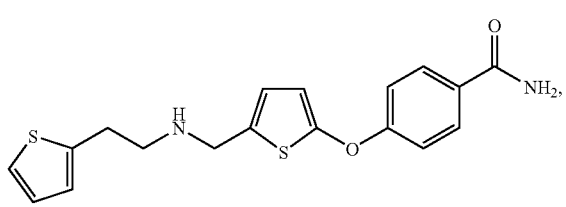

4-{5-[(3,3-Dimethyl-butylamino)-methyl]-thiophen-2-yloxy}-benzamide

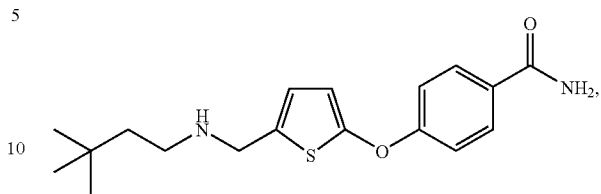

3-Methoxy-4-[5-(phenethylamino-methyl)-thiophen-2-yloxy]-benzamide

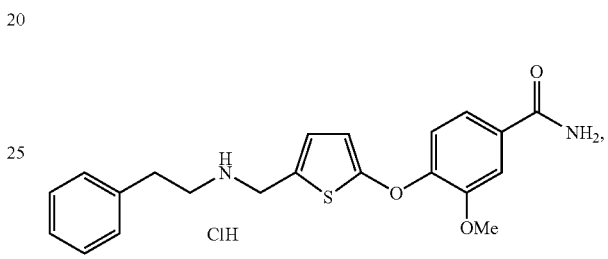

3-Methoxy-4-{5-[(3-methyl-butylamino)-methyl]-thiophen-2-yloxy}-benzamide

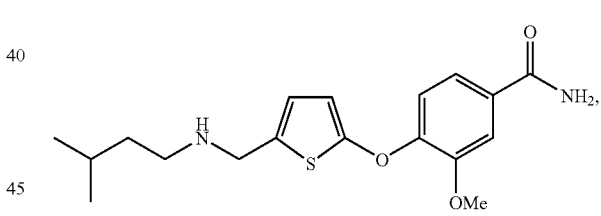

4-[5-(2-Phenethylamino-ethyl)-thiophen-2-yloxy]-benzamide

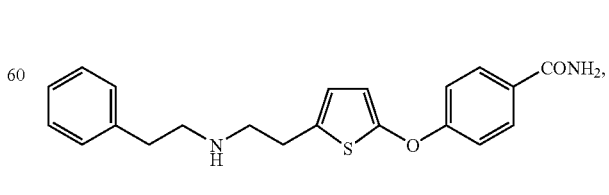

5-{4-[(3-Ethylpentylamino)methyl]phenoxy}thiophene-2-carboxamide

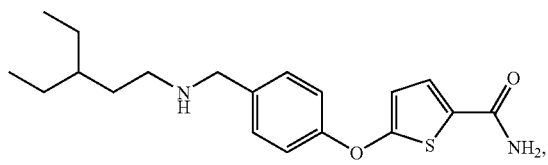

2-{4-[(3-Methylbutylamino)methyl]phenoxy}thiazole-5-carboxamide

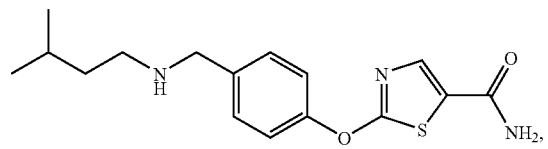

2-(4-{[2-(Tetrahydropyran-4-yl)ethylamino]methyl}phenoxy)thiazole-5-carboxamide

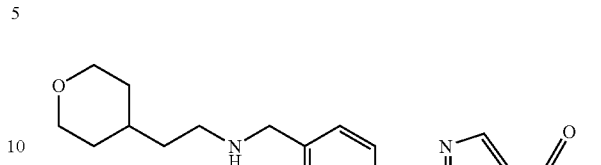

or a pharmaceutically acceptable salt thereof.

2. A pharmaceutical composition comprising a therapeutically effective amount of a compound of claim 1 in association with a carrier, diluent and/or excipient.

\* \* \* \* \*

UNITED STATES PATENT AND TRADEMARK OFFICE
CERTIFICATE OF CORRECTION

PATENT NO. : 7,396,943 B2  Page 1 of 1
APPLICATION NO. : 10/544286
DATED : July 8, 2008
INVENTOR(S) : Dana Rae Benesh et al.

It is certified that error appears in the above-identified patent and that said Letters Patent is hereby corrected as shown below:

On the Title page"
Insert Item -- (60) Related U.S. Application Data
Provisional application no. 60/453,243, filed March 7, 2003. --

Col. 1 lines 2-4, insert the following cross-reference after the title:
-- This application is the national phase application under
35 USC 371, for PCT/US2004/003368, filed March 1, 2004, which,
claims the benefit, under 35 USC 119(e), of US provisional
application 60/453,243, filed March 7, 2003. --

Signed and Sealed this

Seventh Day of December, 2010

David J. Kappos
*Director of the United States Patent and Trademark Office*